(12) United States Patent
LeRoux et al.

(10) Patent No.: US 11,638,102 B1
(45) Date of Patent: Apr. 25, 2023

(54) ACOUSTIC IMPLANT FEEDBACK CONTROL

(71) Applicant: Cochlear Limited, Macquarie University (AU)

(72) Inventors: Thomas LeRoux, Valbonne (FR); James Roy Easter, Lyons, CO (US)

(73) Assignee: Cochlear Limited, Macquarie University (AU)

(*) Notice: Subject to any disclaimer, the term of this patent is extended or adjusted under 35 U.S.C. 154(b) by 818 days.

(21) Appl. No.: 16/444,926

(22) Filed: Jun. 18, 2019

Related U.S. Application Data

(60) Provisional application No. 62/689,665, filed on Jun. 25, 2018.

(51) Int. Cl.
*H04R 25/00* (2006.01)
*A61N 1/36* (2006.01)
*A61N 1/05* (2006.01)

(52) U.S. Cl.
CPC ......... *H04R 25/30* (2013.01); *A61N 1/36038* (2017.08); *H04R 25/505* (2013.01); *H04R 25/604* (2013.01); *A61N 1/0541* (2013.01); *H04R 2225/67* (2013.01); *H04R 2460/01* (2013.01)

(58) Field of Classification Search
CPC ....... H04R 25/00; H04R 25/55; H04R 25/554
See application file for complete search history.

(56) References Cited

U.S. PATENT DOCUMENTS

| | | | |
|---|---|---|---|
| 4,419,995 A * | 12/1983 | Hochmair | A61N 1/36038 607/57 |
| 6,240,192 B1 * | 5/2001 | Brennan | H04R 25/505 381/314 |
| 7,463,745 B2 | 12/2008 | Miller, III | |
| 7,522,738 B2 | 4/2009 | Miller, III | |
| 8,542,855 B2 * | 9/2013 | Elmedyb | H04R 25/552 381/23.1 |
| 8,840,540 B2 | 9/2014 | Miller, III | |
| 9,020,169 B2 | 4/2015 | Meskens | |
| 9,042,996 B2 | 5/2015 | Van Baelen et al. | |
| 9,148,734 B2 | 9/2015 | Hillbratt et al. | |
| 9,654,885 B2 | 5/2017 | Natarajan | |
| 9,729,976 B2 | 8/2017 | Natarajan | |
| 9,769,574 B2 | 9/2017 | Kristensen et al. | |
| 10,575,106 B1 * | 2/2020 | Bergmann | H04R 25/505 |
| 2006/0093173 A1 | 5/2006 | Hamacher et al. | |
| 2015/0382115 A1 * | 12/2015 | Meskens | H04R 25/606 381/326 |
| 2016/0345107 A1 | 11/2016 | Van Dijk et al. | |

* cited by examiner

*Primary Examiner* — Suhan Ni
(74) *Attorney, Agent, or Firm* — Knobbe, Martens, Olson & Bear, LLP

(57) ABSTRACT

An apparatus includes signal processing circuitry configured to generate processed data signals in response at least in part to transducer signals from at least one acoustic transducer and filtering signals, and to transmit the processed data signals via at least one communication channel to an actuating assembly of an auditory prosthesis. The apparatus further includes circuitry configured to monitor one or more of the signal processing circuitry, the processed data signals, and the at least one communication channel, and to generate filtering control signals in response at least in part thereto. The apparatus further includes filtering circuitry configured to generate the filtering signals in response at least in part to the processed data signals and the filtering control signals.

32 Claims, 12 Drawing Sheets

ACOUSTIC IMPLANT FEEDBACK CONTROL

BACKGROUND

Field

The present application relates generally to implantable auditory prostheses, and more specifically systems and methods for feedback control of the acoustic prostheses.

Description of the Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain. Auditory prostheses of various types are widely used to improve the lives of users. Such devices include, for example, hearing aids, cochlear implants, bone conduction implants, middle ear implants, and electro-acoustic devices.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

Forms of these auditory prostheses which are "mostly implantable," "fully implantable," or "totally implantable" have the advantage of allowing the user to have a superior aesthetic result, as the recipient is visually indistinguishable in day-to-day activities from individuals that have not received such devices. Such devices also have a further advantage in generally being inherently waterproof, allowing the recipient to shower, swim, and so forth without needing to take any special measures. Examples of such devices include, but are not limited to, totally implanted cochlear implants ("TICIs") and fully implantable middle ear implants utilizing totally implantable actuators ("TIAs").

While conventional auditory prostheses use externally disposed microphone assemblies, certain mostly, fully, or totally implantable auditory prostheses use subcutaneously implantable microphone assemblies. Such microphone assemblies are configured to be positioned (e.g., in a surgical procedure) beneath the skin and on, within, or proximate to the recipient's skull and at a location that facilitates the receipt of acoustic signals by the microphone assembly once implanted (e.g., at a location between the recipient's skin and skull, rearward and upward of the recipient's ear or in the mastoid region).

SUMMARY

In one aspect disclosed herein, a method is provided which comprises detecting one or more operational states of an auditory prosthesis implanted on or within a recipient. The auditory prosthesis comprises a sound processor utilizing adaptive filtering circuitry to improve an acoustic response of the auditory prosthesis. The method further comprises controlling the sound processor in response at least in part to said detected one or more operational states.

In another aspect disclosed herein, an apparatus is provided which comprises signal processing circuitry configured to generate processed data signals in response at least in part to transducer signals from at least one acoustic transducer and filtering signals, and to transmit the processed data signals via at least one communication channel to an actuating assembly of an auditory prosthesis. The apparatus further comprises monitoring circuitry configured to monitor one or more of the signal processing circuitry, the processed data signals, and the at least one communication channel, and to generate monitoring signals in response thereto. The apparatus further comprises control circuitry configured to receive the monitoring signals and to generate filtering control signals in response at least in part thereto. The apparatus further comprises filtering circuitry configured to generate the filtering signals in response at least in part to the processed data signals and the filtering control signals.

In still another aspect disclosed herein, an apparatus is provided which comprises at least one sound processor of an auditory prosthesis. The at least one sound processor is configured to receive microphone output signals from at least one microphone assembly of the auditory prosthesis. The microphone output signals are indicative of sound received by the at least one microphone assembly. The at least one sound processor is further configured to estimate a feedback contribution portion of the microphone output signals. The at least one sound processor is further configured to detect one or more error conditions indicative of errors in the estimated feedback contribution portion. The at least one sound processor is further configured to select an operational state of the at least one sound processor in response to the detected one or more error conditions.

BRIEF DESCRIPTION OF THE DRAWINGS

Embodiments are described herein in conjunction with the accompanying drawings, in which.

DETAILED DESCRIPTION

Certain embodiments described herein provide a system and method for controlling adaptive filtering circuitry of "partially implantable," "semi-implantable," "mostly implantable," "fully implantable," or "totally implantable" auditory prostheses. While adaptive filtering circuitry is used to improve the acoustic response of auditory prostheses during normal operations, under some conditions (e.g., communications between the sound processor and the implanted actuator of the auditory prosthesis are not operational; sounds being processed are such that the adaptive filtering circuitry is unable to determine feedback filter coefficient values within predetermined time periods and/or predetermined ranges), the adaptive filtering circuitry may degrade the acoustic response of the auditory prosthesis by generating unwanted acoustic effects (e.g., artifacts, noise, oscillations, and/or instabilities).

Certain embodiments described herein advantageously provide a system and method configured to provide the auditory prosthesis with information regarding the status of the communication channel between the sound processor and the actuator and/or regarding the data signals transmitted via the communication channel. For example, the auditory prosthesis can monitor one or more of: telemetry from the actuator; current and/or power consumption by the communication channel; data signals being transmitted to the actuator via the communication channel; filter coefficient values generated by the adaptive filtering circuitry. The auditory prosthesis can utilize this information to control the adaptive filtering circuitry for optimized performance or to control other components of the auditory prosthesis (e.g., other aspects of the signal processing or device state, such as triggering a sleep mode).

The teachings detailed herein are applicable, in at least some embodiments, to any type of auditory prosthesis utilizing an implantable actuator assembly including but not limited to: electro-acoustic electrical/acoustic systems, cochlear implant devices, implantable hearing aid devices, middle ear implant devices, bone conduction devices (e.g., active bone conduction devices; passive bone conduction devices, percutaneous bone conduction devices; transcutaneous bone conduction devices), Direct Acoustic Cochlear Implant (DACI), middle ear transducer (MET), electro-acoustic implant devices, other types of auditory prosthesis devices, and/or combinations or variations thereof, or any other suitable hearing prosthesis system with or without one or more external components. Embodiments can include any type of auditory prosthesis that can utilize the teachings detailed herein and/or variations thereof. In some embodiments, the teachings detailed herein and/or variations thereof can be utilized in other types of prostheses beyond auditory prostheses.

Figure 1:
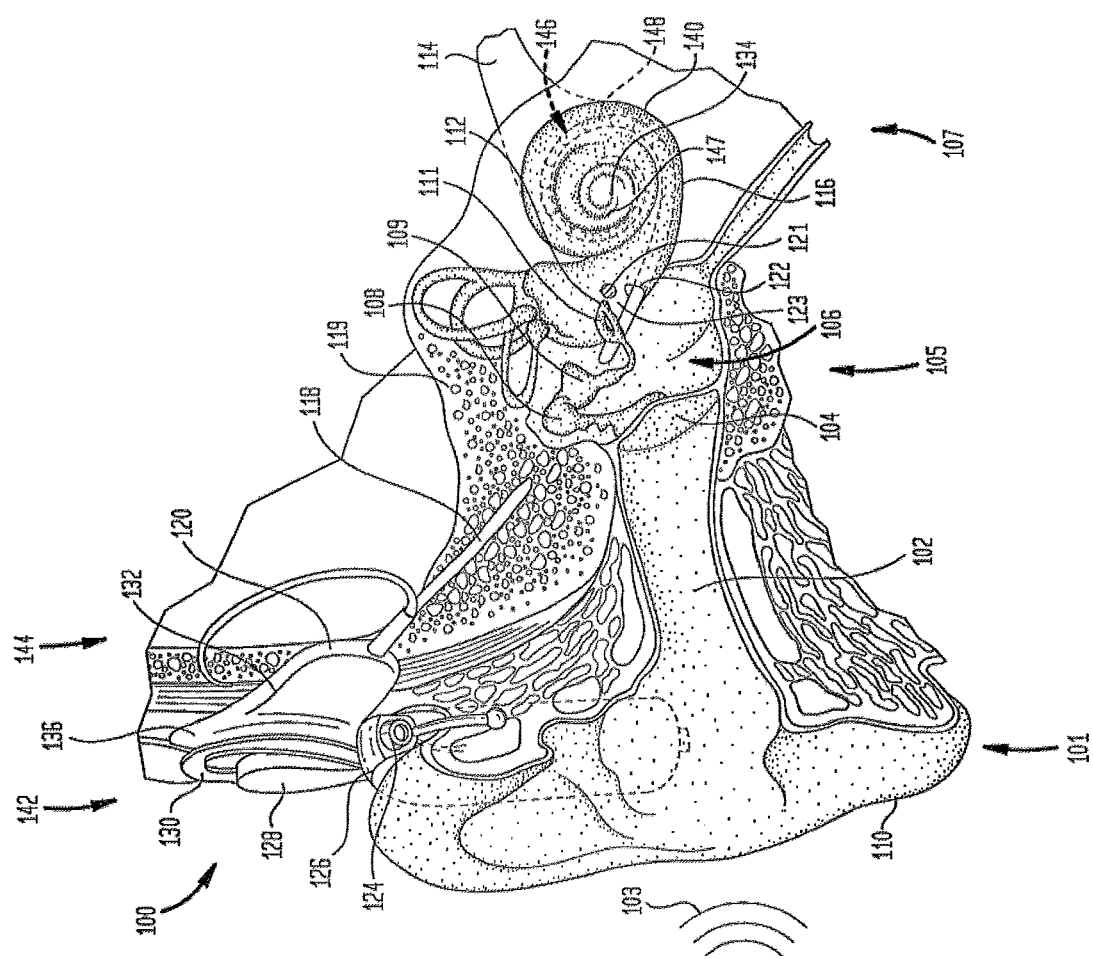
FIG. 1 is a perspective view of an example cochlear implant auditory prosthesis implanted in a recipient in accordance with certain embodiments described herein.

FIG. 1 is a perspective view of an example cochlear implant auditory prosthesis 100 implanted in a recipient in accordance with certain embodiments described herein. The example auditory prosthesis 100 is shown in FIG. 1 as comprising an implanted stimulator unit 120 (e.g., an actuator) and an external microphone assembly 124 (e.g., a partially implantable cochlear implant). An example auditory prosthesis 100 (e.g., a totally implantable cochlear implant) in accordance with certain embodiments described herein can replace the external microphone assembly 124 shown in FIG. 1 with a subcutaneously implantable assembly comprising an acoustic transducer (e.g., microphone), as described more fully herein.

As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative embodiments of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted embodiment, by the recipient's auricle 110. The sound processing unit 126 generates encoded signals, sometimes referred to herein as encoded data signals, which are provided to the external transmitter unit 128 (e.g., via a cable).

As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some embodiments, the internal receiver unit 132 and the stimulator unit 120 are hermetically sealed within a biocompatible housing. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal receiver unit 132 and the stimulator unit 120 are hermetically sealed within a biocompatible housing, sometimes collectively referred to as a stimulator/receiver unit. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some embodiments, the electrode assembly 118 may be implanted at least in the basal region 116, and sometimes further. For example, the electrode assembly 118 may extend towards apical end of cochlea 140, referred to as cochlea apex 134. In certain circumstances, the electrode assembly 118 may be inserted into the cochlea 140 via a cochleostomy 122. In other circumstances, a cochleostomy may be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

Figure 2A:
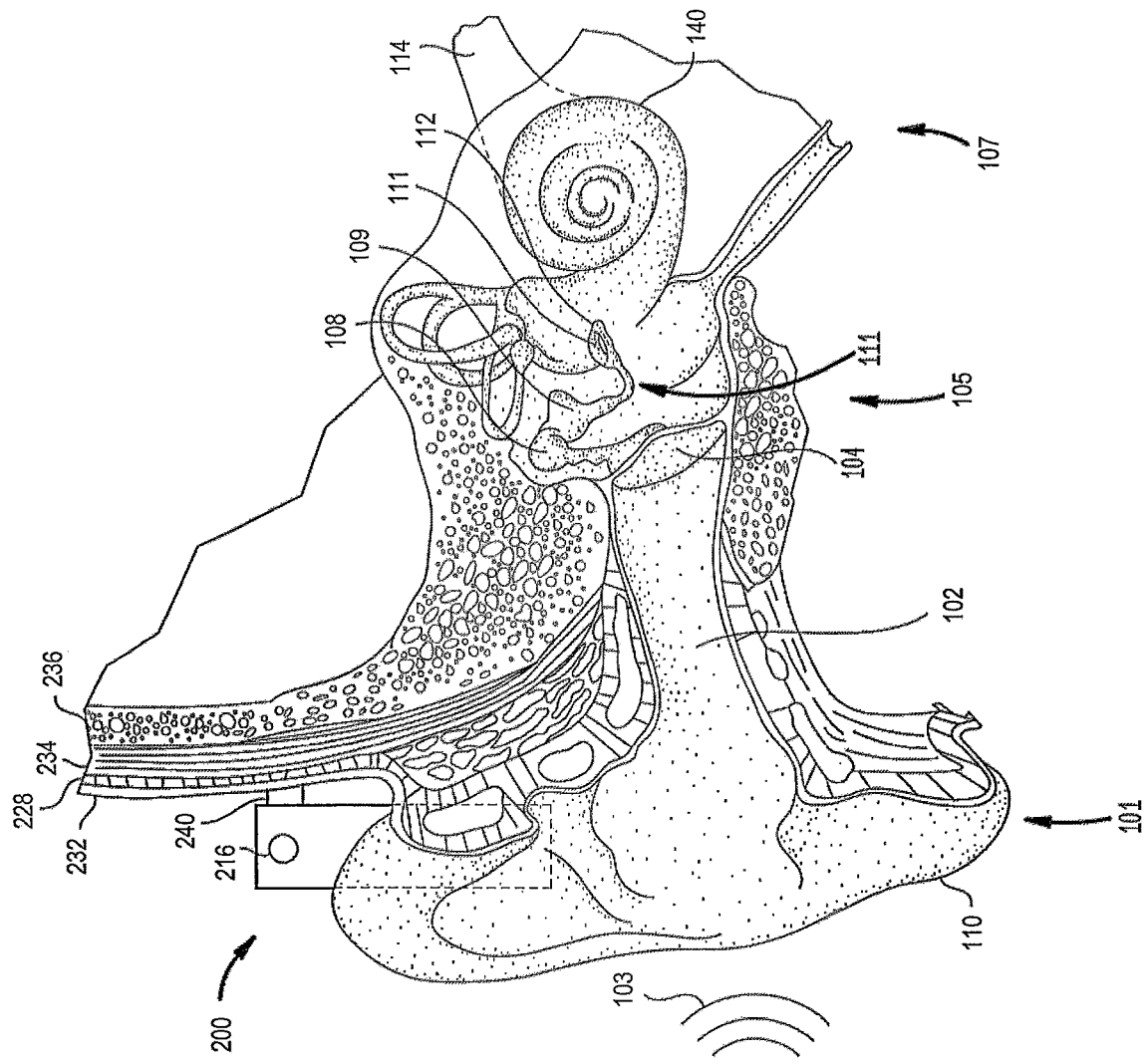
FIG. 2A is a perspective view of an example percutaneous bone conduction auditory prosthesis implanted in a recipient in accordance with certain embodiments described herein.
Figure 2B:
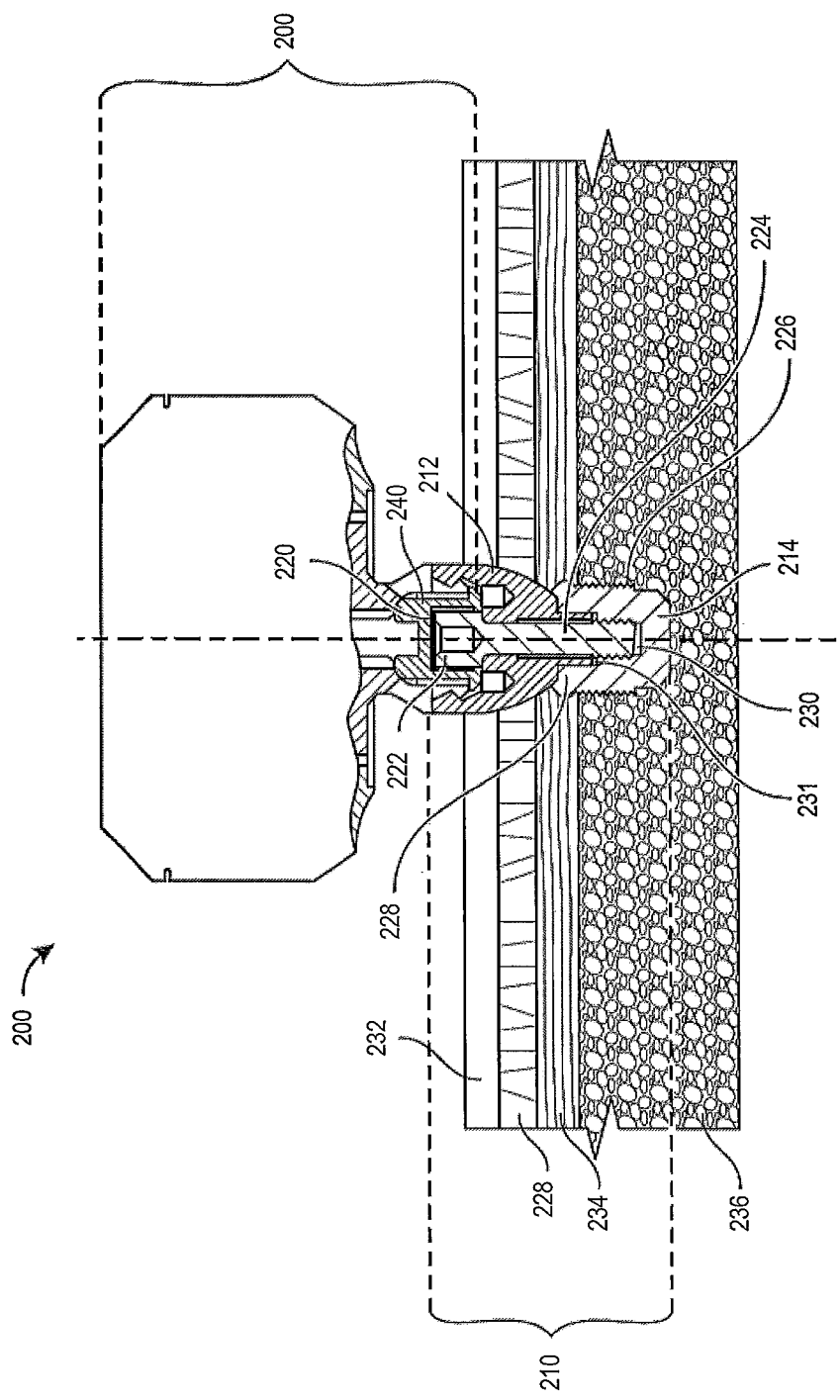
FIG. 2B depicts a side view of a portion of an example percutaneous bone conduction auditory prosthesis in accordance with certain embodiments described herein.

FIG. 2A is a perspective view of an example percutaneous bone conduction auditory prosthesis 200 implanted in a recipient in accordance with certain embodiments described herein. FIG. 2B depicts a side view of a portion of an example percutaneous bone conduction auditory prosthesis 200 in accordance with certain embodiments described herein. As shown in FIG. 2A, the auditory prosthesis 200 is positioned behind the outer ear 101 of the recipient.

In certain embodiments, the auditory prosthesis 200 comprises an operationally removable component 205 and a bone conduction implant 210, with the operationally removable component 205 operationally releasably coupled to the bone conduction implant 210. By operationally releasably coupled, it is meant that it is releasable in such a manner that the recipient can relatively easily attach and remove the operationally removable component 205 during normal use of the auditory prosthesis 200, repeatedly if desired. Such releasable coupling is accomplished via a coupling apparatus 240 of the operationally removable component 205 and a corresponding mating apparatus of the bone conduction implant 210.

The bone conduction implant 210 comprises a percutaneous abutment 212, a bone fixture 214 (hereinafter sometimes referred to as the fixture), and an abutment screw 220. The abutment 212 is configured to be rigidly attached (e.g., vibrationally connected) to the fixture 214 via the abutment screw 220, and the fixture 214 is configured to be fixed to (e.g., screwed into) the recipient's skull bone 236. For example, the fixture 214 can be formed from a single piece of material (e.g., titanium) and comprises outer screw threads 226 forming a male screw which is configured to be installed into the skull bone 236, a flange 228 configured to function as a stop when the fixture 214 is implanted into the skull bone 236, and an inner upper bore 231 configured to receive a bottom portion of the abutment 212.

The abutment 212 extends from the fixture 214, through muscle 234, fat 228, and skin 232 so that the coupling apparatus 240 can be attached thereto to facilitate efficient transmission of mechanical force. The abutment screw 220 comprises a screw head 222 and an elongate coupling shaft 224 having screw threads configured to mate with screw threads of an inner lower bore 230 of the fixture 214. Other bone conduction implants 210 (e.g., comprising abutments 212, fixtures 214, and/or abutment screws 220 of any type, size/having any geometry) are also compatible with certain embodiments described herein.

The operationally removable component 205 includes the acoustic transducer 216 (e.g., a microphone), a sound processor (e.g., an electronics module), and an actuating assembly (e.g., a vibrating electromagnetic actuator; a vibrating piezoelectric actuator; other type of vibrating actuator) configured to generate acoustic vibrations. More particularly, the acoustic transducer 216 converts received sound signals 107 into electrical signals which are processed by the electronics module (e.g., which can include a sound processing circuit, control electronics, transducer drive components, and a variety of other elements). The electronics module is configured to respond to the electrical signals by generating control signals which cause the actuator to vibrate, generating a mechanical output force in the form of acoustic vibrations that is delivered to the skull of the recipient via the bone conduction implant 210. In other words, the operationally removable component 205 converts the received sound signals 107 into mechanical motion using the actuator to impart vibrations to the recipient's skull. Delivery of this output force causes motion or vibration of the recipient's skull, thereby activating the hair cells in the recipient's cochlea 140 via cochlea fluid motion. While FIGS. 2A and 2B illustrate an example bone conduction auditory prosthesis 200 utilizing an external acoustic transducer 216, external sound processor, and external actuator, in certain other embodiments, one or more of the acoustic transducer 216, sound processor, and actuator can be implantable on or within the recipient.

Figure 3:
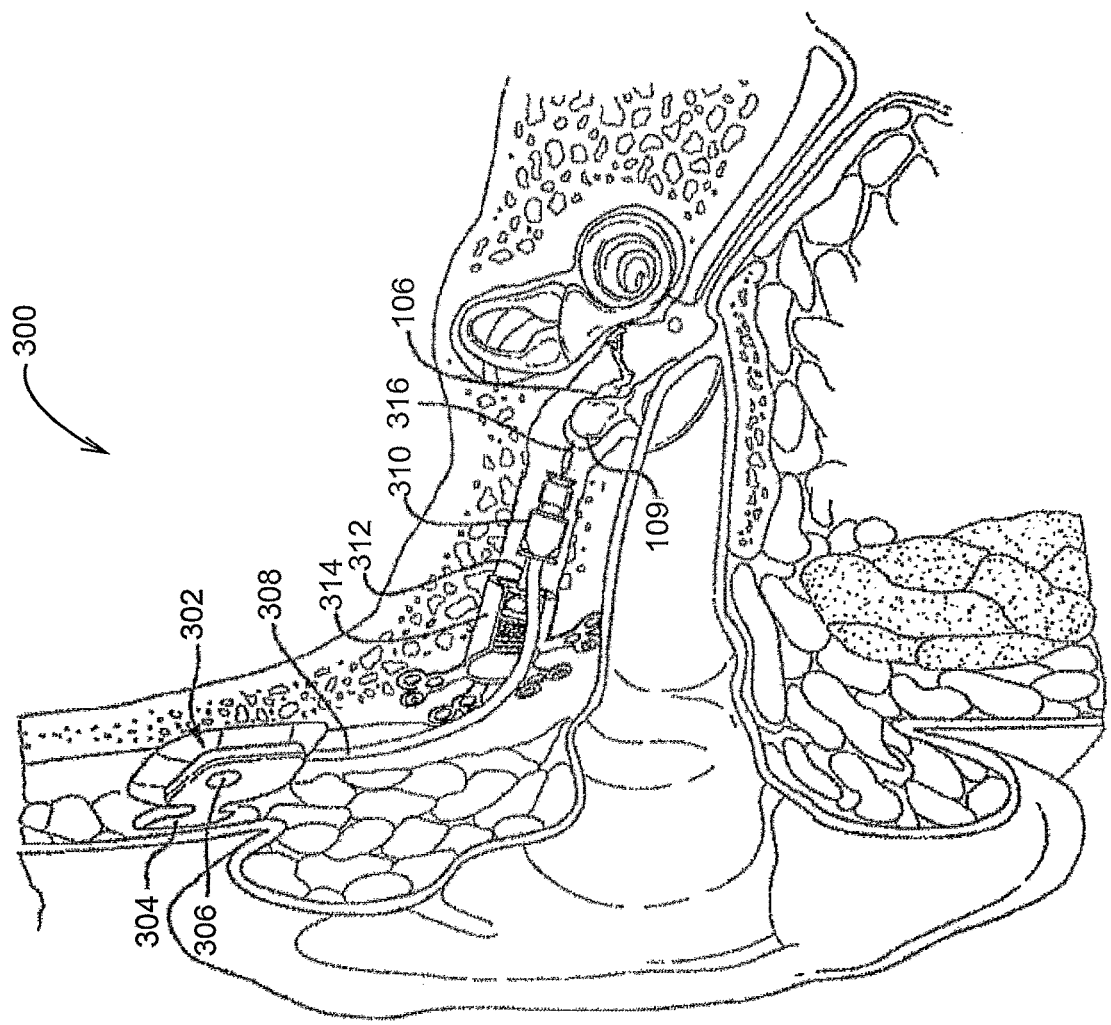
FIG. 3 is a perspective view of an example fully implantable middle ear implant auditory prosthesis implanted in a recipient, utilizing a totally implantable actuator ("TIA") in accordance with certain embodiments described herein.

FIG. 3 schematically illustrates a perspective view of an example fully implantable auditory prosthesis 300 (e.g., fully implantable middle ear implant), implanted in a recipient, utilizing a totally implantable actuator ("TIA") in accordance with certain embodiments described herein. The example auditory prosthesis 300 of FIG. 3 comprises a biocompatible microphone assembly 302 (e.g., comprising an implantable capsule) located subcutaneously (e.g., beneath the recipient's skin and on a recipient's skull). The microphone assembly 302 includes a signal receiver 304 (e.g., comprising a coil element) and an acoustic transducer 306 (e.g., comprising an electret diaphragm or a piezoelectric diaphragm) that is positioned to receive acoustic signals through the recipient's overlying tissue. The microphone assembly 302 may further be utilized to house a number of components of the fully implantable auditory prosthesis 300. For example, the microphone assembly 302 can include an energy storage device and a signal processor (e.g., a sound processing unit). Various additional processing logic and/or circuitry components can also be included in the microphone assembly 302 as a matter of design choice.

For the example auditory prosthesis 300 shown in FIG. 3, the signal processor of the implantable microphone assembly 302 is in operative communication (e.g., electrically interconnected via a wire 308) with an actuator 310 (e.g., TIA comprising a transducer configured to generate mechanical vibrations in response to electrical signals from the microphone assembly 302). In certain embodiments, the example auditory prosthesis 100, 200 shown in FIGS. 1 and 2A-2B can comprise an implantable microphone assembly, such as the microphone assembly 302 shown in FIG. 3. For such an example auditory prosthesis 100, the signal processor of the implantable microphone assembly 302 can be in operative communication (e.g., electrically interconnected via a wire) with the stimulator unit of the main implantable component 120. In certain embodiments, at least one of the microphone assembly and the signal processor (e.g., a sound processing unit) is implanted on or within the recipient.

The actuator 310 of the example auditory prosthesis 300 shown in FIG. 3 is supportably connected to a positioning system 312, which in turn, is connected to a bone anchor 314 mounted within the recipient's mastoid process (e.g., via a hole drilled through the skull). The actuator 310 includes a connection apparatus 316 for connecting the actuator 310 to the ossicles 106 of the recipient. In a connected state, the connection apparatus 316 provides a communication path for acoustic stimulation of the ossicles 106 (e.g., through transmission of vibrations from the actuator 310 to the incus 109).

During normal operation, ambient acoustic signals (e.g., ambient sound) impinge on the recipient's tissue and are received transcutaneously at the acoustic transducer 306. Upon receipt of the transcutaneous signals, a signal processor within the microphone assembly 302 processes the signals to provide a processed audio drive signal via wire 308 to the actuator 310. As will be appreciated, the signal processor may utilize digital processing techniques to provide frequency shaping, amplification, compression, and other signal conditioning, including conditioning based on recipient-specific fitting parameters. The audio drive signal causes the actuator 310 to transmit vibrations at acoustic frequencies to the connection apparatus 316 to affect the desired sound sensation via mechanical stimulation of the incus 109 of the recipient.

The subcutaneously implantable microphone assembly 302 is configured to respond to auditory signals (e.g., sound; pressure variations in an audible frequency range) by generating output signals (e.g., electrical signals; optical signals; electromagnetic signals) indicative of the auditory signals received by the microphone assembly 302, and these output signals are used by the auditory prosthesis 100, 200, 300 to generate stimulation signals which are provided to the recipient's auditory system. To compensate for the decreased acoustic signal strength reaching the microphone assembly 302 by virtue of being implanted, the diaphragm of an implantable microphone assembly 302 is configured to provide higher sensitivity than are external non-implantable microphone assemblies (e.g., by using diaphragms that are larger than diaphragms for external non-implantable microphone assemblies).

However, this heightened acoustic sensitivity also makes the implantable microphone assembly more sensitive to other signals or contributions which contribute noise or other undesirable effects to the stimulation signals. These non-ambient noise signals, in at least some embodiments, are not of an energy level and/or frequency to be audible at a location away from the recipient, but still result in vibrations detected by the acoustic transducer 306 (e.g., vibrations of the diaphragm of the acoustic transducer 306). For example, with regard to auditory prostheses 100, 200, 300, biological sources may cause vibrations (e.g., biological noise) which are conducted to the implanted microphone assembly 302 through the recipient's tissue, and are amplified by the auditory prosthesis 100, 200, 300. Such biological sources may include, without limitation, vibrations caused by speaking, chewing, movement of the recipient's tissue over the microphone assembly 302 (e.g., caused by the recipient turning their head), and the like.

For another example, with regard to auditory prostheses 300 (e.g., utilizing TIAs), upon operation of the actuator 310, vibrations are applied to the incus 109, but such vibrations are also applied to the bone anchor 314. The vibrations applied to the bone anchor 314 are likewise conveyed to the recipient's skull from where they may be conducted to the microphone assembly 302 and/or to tissue overlying the acoustic transducer 306. Accordingly such vibrations may be applied to the acoustic transducer 306 and thereby included in the output response of the microphone assembly 302. Stated otherwise, mechanical feedback from operation of the actuator 310 may be received by the acoustic transducer 306 of the implanted microphone assembly 302 via a feedback loop formed through the recipient's tissue. Further, application of vibrations to the incus 109 may also vibrate the eardrum 104, thereby causing sound pressure waves, which may pass through the ear canal 102 where they may be received by the acoustic transducer 306 of the implanted microphone assembly 302 as ambient sound.

Each of the example auditory prostheses 100, 200 shown in FIGS. 1 and 2A-2B utilizes an external acoustic transducer (e.g., microphone 124; microphone 216) and the auditory prosthesis 300 shown in FIG. 3 utilizes a subcutaneously implantable acoustic transducer 306. In certain embodiments described herein, the auditory prosthesis 100, 200, 300 utilizes one or more acoustic transducers that are positioned external to the recipient and/or one or more implanted acoustic transducers on or within the recipient. In certain embodiments, an external acoustic transducer can be used to supplement an implantable acoustic transducer of the auditory prosthesis 100, 200, 300. Thus, the teachings detailed herein and/or variations thereof can be utilized with any type of external or implantable microphone arrangement, and the acoustic transducers shown in FIGS. 1-3 are merely illustrative.

In certain embodiments, the auditory prosthesis 100, 200, 300 includes adaptive filtering circuitry (e.g., an adaptive feedback canceler) configured to mitigate (e.g., avoid; reduce; inhibit; cancel) unwanted contributions to the stimulation signals provided to the recipient's auditory system (e.g., feedback contributions due to acoustic or vibrational signals generated by the implanted actuator and received by the implanted microphone assembly; contributions due to various non-acoustic effects on the implanted microphone assembly). This adaptive filtering circuitry is configured to improve the acoustic response of the auditory prosthesis 100, 200, 300 during normal operations by estimating the unwanted contributions (e.g., estimating the unwanted contributions due to feedback along an estimated feedback path) and creating a filter used to create a cancelation signal to mitigate (e.g., avoid; reduce; inhibit; cancel) these estimated contributions so they do not unduly affect the data signals transmitted to the actuator.

However, under some conditions in which the estimated contributions deviate significantly from the actual contributions, the adaptive filtering circuitry can degrade the acoustic response of the auditory prosthesis 100, 200, 300 by generating unwanted acoustic effects (e.g., artifacts, noise, oscillations, and/or instabilities). For example, under conditions during which the communications between the signal processor (e.g., sound processing unit) and the implanted actuator are non-operational, the feedback contributions estimated by the adaptive filtering circuitry can be incorrect since the data signals from the signal processor are not reaching the actuator, so the actuator does not generate stimulation signals and there is actually no feedback (e.g., the feedback loop is interrupted), unbeknownst to the signal processor which continues to output the data signals. Examples of non-operational communications include but are not limited to: one or more broken or lost communication channels (e.g., one or more wireless radio-frequency links; one or more wireless inductive links; one or more wired links) between the signal processor and the implanted actuator; signal processor is removed from the recipient (e.g., sound processor of a bone conduction auditory prosthesis disconnected from the implant); signal processor is in wireless communication with a different implanted actuator (e.g., with an actuator on a different ear of the recipient having an actuator on each ear); interference of the one or more radio-frequency wireless communication channels.

During periods that the communications are non-operational and the adaptive filtering circuitry continues operation, the sound processor does not have full control of the audio output state at the actuator and the filter coefficient values generated by the adaptive filtering circuitry do not correspond to physical reality (e.g., the feedback cancellation algorithm can be unstable). Upon the communications between the signal processor and the actuator being re-established, the filter coefficient values initially used by the adaptive filtering circuitry can create unwanted acoustic effects (e.g., artifacts, noise, oscillations, and/or instabilities) in the data signals.

For another example, under conditions during which the ambient sounds have certain characteristics (e.g., a loud impulse sound), the circuitry of the signal processor (e.g., including the adaptive filtering circuitry) and/or the actuator can undergo a reset for a short period of time during which the data signals and/or stimulation signals are muted (e.g., a few milliseconds) and then resume. Since fast adaptation speeds are often used in the adaptive filtering circuitry, the estimated contributions are incorrect during the muted period and are incorrect when operation resumes. This behavior can repeat multiple times as the ambient sounds get lower and/or the signal processor and/or actuator adapts to the louder ambient sound. As a result, the adaptive filtering circuitry can be unable to determine appropriate filter coefficient values within predetermined time periods and/or within predetermined ranges, and the sharp transitions experienced by the recipient (e.g., oscillating between loud sounds to silence) as the adaptive filtering circuitry adjusts to the ambient sounds can be unwanted acoustic effects which are disturbing to the recipient.

Certain embodiments described herein are configured to provide the sound processor with information regarding the status of the one or more communication channels between the sound processor and the actuator of the auditory prosthesis 100, 200, 300 and/or regarding the data signals transmitted via the one or more communication channels. The sound processor is configured to utilize this information to control the adaptive filtering circuitry for optimized performance. For example, upon detecting that the one or more communication channels are lost such that feedback cannot exist, the operation of the adaptive filtering circuitry can be modified (e.g., stopped; reduced adaptation speed; changed adaptation type; utilize previously-stored filter coefficient values; reset a state of one or more variables or buffers used by the adaptive filtering circuitry). The modifications of the operation of the adaptive filtering circuitry can depend on the length of time that the one or more communication channels have been lost.

As described herein, certain embodiments used in conjunction with a fully implantable auditory prosthesis advantageously allow detection of undesirable operational states of the adaptive filtering circuitry (e.g., feedback mitigation algorithm) operating in combination with an implantable microphone (e.g., instabilities resulting from sudden changes of skin thickness resulting from a change in posture or filter coefficient values outside predetermined ranges resulting from external pressure changes experienced by the microphone) and permits the auditory prosthesis to respond to such detected undesirable operational states in a manner that advantageously minimizes discomfort to the recipient (e.g., by suppressing audio artifacts or lowering volume for a specified time period). Certain embodiments used in conjunction with a fully implantable auditory prosthesis with an external accessory (e.g., external microphone or streaming audio source) advantageously allow detection of undesirable operational states of the implantable microphone, or with the external accessory (e.g., microphone or streaming audio source). For example, upon detecting an undesirable operational state with regard to the use of one of the implantable microphone and the external accessory, the auditory prosthesis can automatically switch to instead using the other.

Figure 4A:
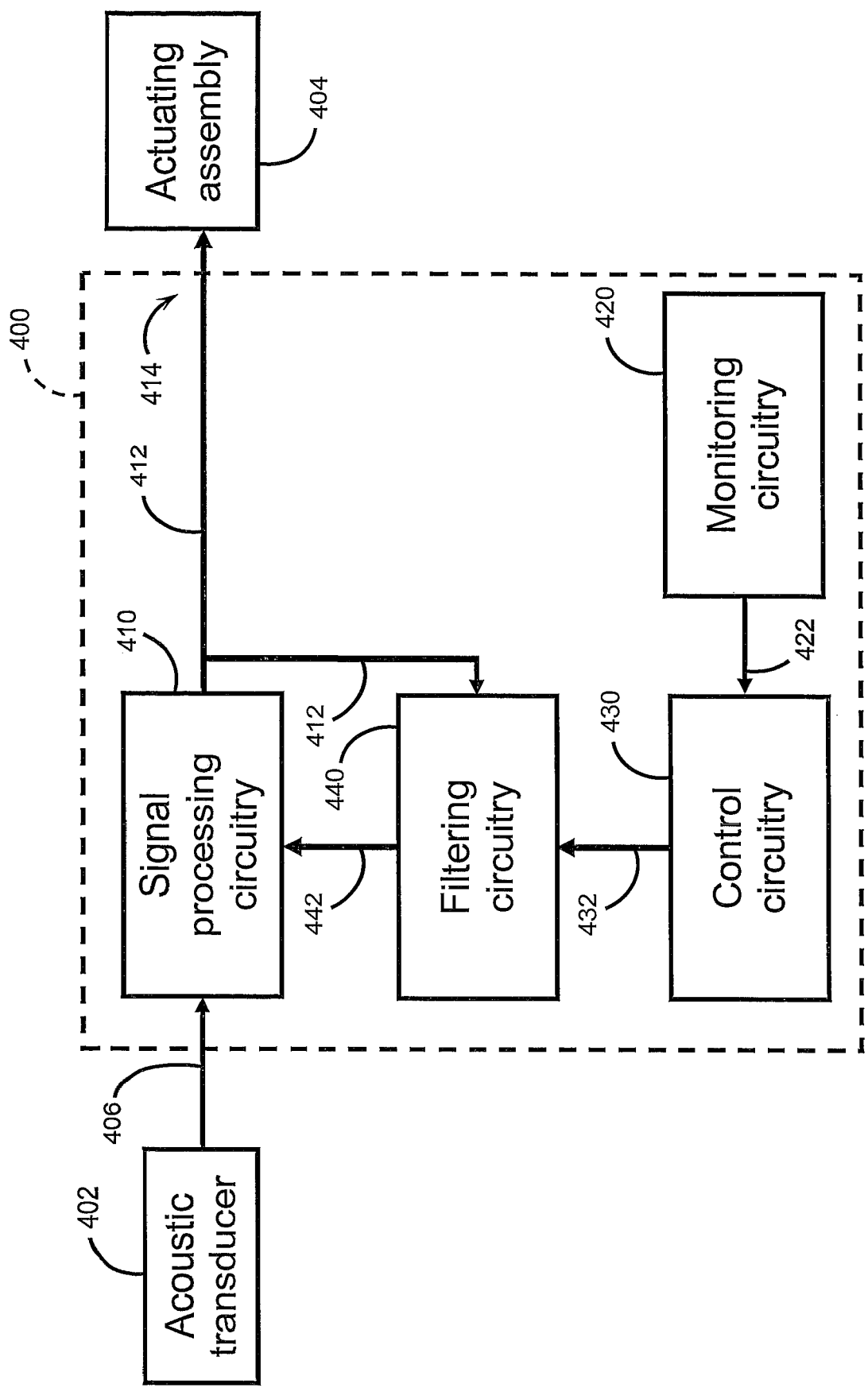
FIG. 4A schematically illustrates an example apparatus in accordance with certain embodiments described herein.

FIG. 4A schematically illustrates an example apparatus 400 in accordance with certain embodiments described herein. The apparatus 400 comprises signal processing circuitry 410 configured to generate processed data signals 412 in response at least in part to transducer signals 406 from at least one acoustic transducer 402 (e.g., microphone assembly, either external to the recipient or implanted on or within the recipient) and filtering signals 442. The signal processing circuitry 410 is further configured to transmit the processed data signals 412 via at least one communication channel 414 to an actuating assembly 404 (e.g., comprising an implanted actuator; stimulator unit 120; actuator 310) of an auditory prosthesis 100, 200, 300. The apparatus 400 further comprises monitoring circuitry 420 configured to monitor one or more of the signal processing circuitry 410, the processed data signals 412, and the at least one communication channel 414, and to generate monitoring signals 422 in response thereto. The apparatus 400 further comprises control circuitry 430 configured to receive the monitoring signals 422 and to generate filtering control signals 432 in response at least in part thereto. The apparatus 400 further comprises filtering circuitry 440 configured to generate the filtering signals 442 in response at least in part to the processed data signals 412 and the filtering control signals 432. The at least one acoustic transducer 402 is exposed to ambient acoustic signals received from a source that is external to the recipient.

In certain embodiments, the apparatus 400 is a component of an auditory prosthesis system, examples of which include but are not limited to: a cochlear implant system, a bone conduction implant system (e.g., active bone conduction system; passive bone conduction system, percutaneous bone conduction system; transcutaneous bone conduction system), a Direct Acoustic Cochlear Implant (DACI) system, a middle ear implant system, a middle ear transducer (MET) system, an electro-acoustic implant system, another type of auditory prosthesis system, and/or combinations or variations thereof. For example, in a cochlear implant system that does not comprise an acoustic feedback loop since the actuating assembly 404 does not generate acoustic feedback, the apparatus 400 can be configured to be responsive to circumstances in which communications between the apparatus 400 and the actuating assembly 404 is lost or where operation of the filtering circuitry 440 of the apparatus 400 is improper (e.g., under conditions during which the ambient sounds result in the filtering circuitry 440 being unable to determine appropriate filter coefficient values within predetermined time periods and/or within predetermined ranges). For another example, in an electro-acoustic cochlear implant system in which the apparatus 400 is in communication with the actuating assembly 404 and with an in-ear speaker (e.g., a hearing aid), the filtering circuitry 440 can comprise an active feedback canceler configured to estimate a feedback contribution portion of the transducer signals 406 (e.g., based at least in part on accelerometer signals from at least one accelerometer) and to generate filtering signals 442 indicative of the estimated feedback contribution portion.

In certain embodiments, the apparatus 400 comprises a signal processing unit (e.g., external or implantable) of an auditory prosthesis system (e.g., auditory prosthesis 100, 200, 300). For example, the signal processing unit can comprise a digital signal processor ("DSP") having one or more microprocessors or application-specific integrated circuits ("ASICs") which comprise one or more of the signal processing circuitry 410, monitoring circuitry 420, control circuitry 430, and filtering circuitry 440. In certain embodiments, each of the signal processing circuitry 410, monitoring circuitry 420, control circuitry 430, and filtering circuitry 440 comprises at least one processor (e.g., microelectronic circuitry; one or more microprocessors or ASICs) and at least one storage device (e.g., non-volatile memory; flash memory) operatively coupled to the at least one processor. In certain embodiments, two or more of the signal processing circuitry 410, monitoring circuitry 420, control circuitry 430, and filtering circuitry 440 comprise the same at least one processor and/or the same at least one storage device.

In certain embodiments, the at least one acoustic transducer 402 of the auditory prosthesis 100, 200, 300 comprises at least one microphone assembly (e.g., external or implantable) comprising the at least one acoustic transducer 402 and configured to respond to sound received by the at least one acoustic transducer 402 by generating the transducer signals 406 which are indicative of the received sound. In certain embodiments, the actuating assembly 404 of the auditory prosthesis 100, 200, 300 comprises an implanted actuator (e.g., implanted stimulator unit 120; implanted actuator 310).

Figure 4B:
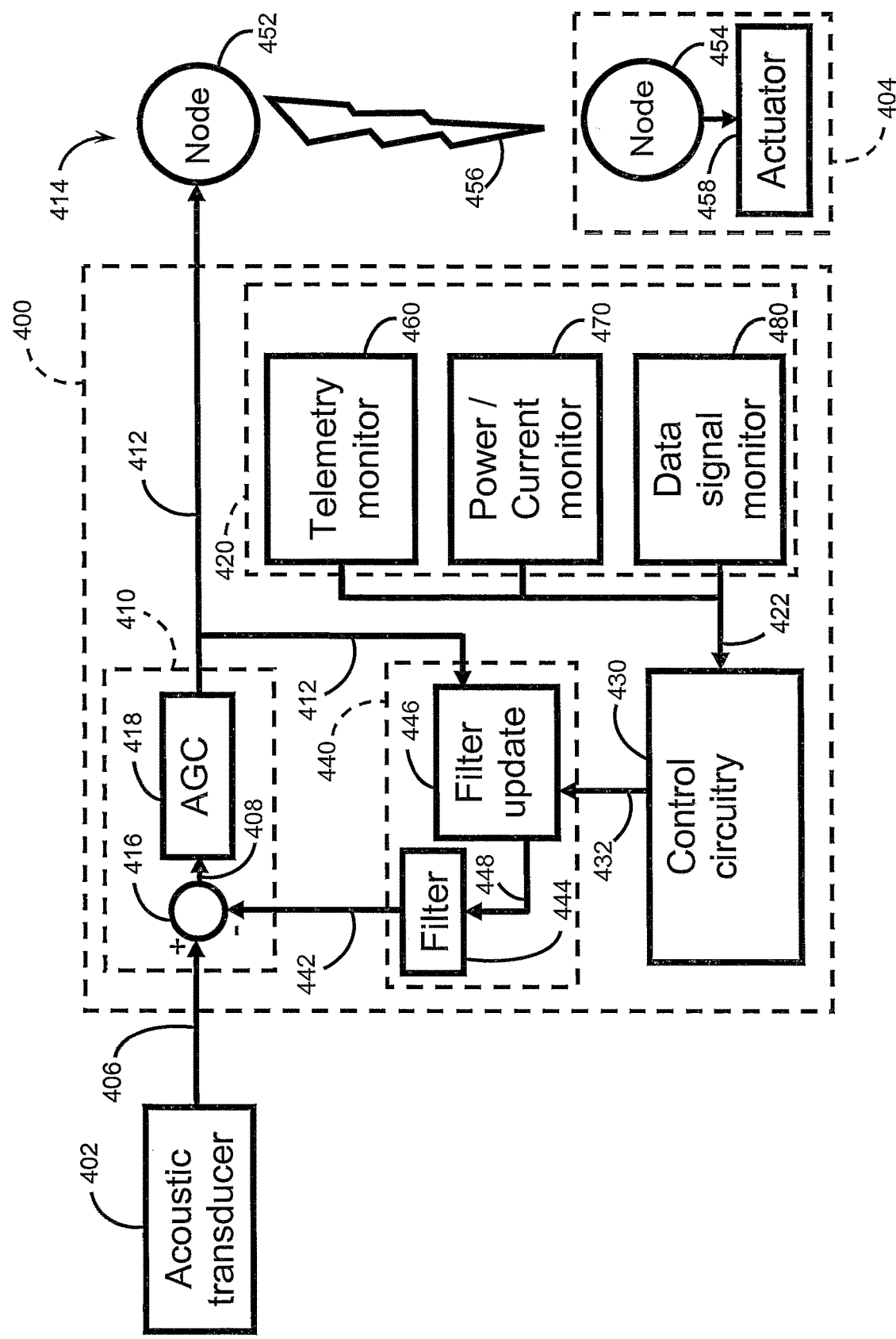
FIG. 4B schematically illustrates another example apparatus in accordance with certain embodiments described herein.

FIG. 4B schematically illustrates another example apparatus 400 in accordance with certain embodiments described herein. The signal processing circuitry 410 comprises an adder 416 and an automatic gain controller ("AGC") 418. The adder 416 is configured to receive the transducer signals 406 from the at least one acoustic transducer 402 and the filtering signals 442 from the filtering circuitry 440. The resultant signals 408 are received by the AGC 418 and represent net audio signals (e.g., cleansed or clean signals) with a reduced feedback or biological noise component.

The AGC 418 is configured to receive the resultant signals 408 after the filtering signals 442 have been subtracted out from the transducer signals 406 at the adder 416 and to further process the resultant signals 408 to generate the processed data signals 412. The AGC 418 of certain embodiments comprises at least one processor (e.g., microelectronic circuitry) and at least one storage device (e.g., non-volatile memory; flash memory) operatively coupled to the at least one processor. The at least one processor comprises gain circuitry configured to adjust a gain applied to the resultant signals 408 and the at least one storage device comprises information (e.g., gain coefficient values) to be used by the at least one processor to adjust the applied gain.

As schematically illustrated by FIG. 4B, the filtering circuitry 440 of certain embodiments comprises a filter circuit 444 and a filter update circuit 446. The filter circuit 444 of certain embodiments comprises one or more adjustable filters, such as, by way of example only and not by way of limitation, one or more adaptive filters (e.g., least-mean-square (LMS) adaptive filters; normalized least-mean-square (NLMS) adaptive filters; recursive least square (RLS) adaptive filters; filters working in the time-domain, frequency-domain, or through any filterbanks). Other embodiments can be implemented using adjustable filters that are not adaptive filters. Any filtering configuration can enable the teachings detailed herein and/or variations thereof to be practiced can be utilized in at least some embodiments. The filter update circuit 446 is configured to receive the processed data signals 412 from the signal processing circuitry 410 and the filtering control signals 432 from the control circuitry 430 and to generate filter coefficient values 448 to be used by the filter circuit 444 in generating the filtering signals 442. The filter update circuit 446 of certain embodiments comprises at least one processor (e.g., microelectronic circuitry) running an adaption algorithm to control the filter circuit 444 and at least one storage device (e.g., non-volatile memory; flash memory) operatively coupled to the at least one processor and configured to store information (e.g., predetermined filter coefficient values 448) to be used by the at least one processor. Various example configurations for adaptive filtering for an auditory prosthesis 100, 200, 300 (e.g., comprising an implantable microphone assembly)

compatible with certain embodiments described herein are described by U.S. Pat. No. 8,840,540 and U.S. Publ. Pat. Appl. No. 2016/0345107.

As schematically illustrated by FIG. 4B, in certain embodiments, the at least one communication channel 414 (e.g., an inductive wireless link; a radio frequency (RF) wireless link; a wired link) comprises a first node 452 (e.g., connector; coil; antenna) in communication with a second node 454 (e.g., connector; coil; antenna) of the actuating assembly 404. For example, the first node 452 can receive the processed data signals 412 from the signal processing circuitry 410 and can transmit signals 456 that are indicative of the processed data signals 412 to the second node 454. For example, the signals 456 can comprise wireless signals that are wirelessly transmitted from the first node 452 to the second node 454. The second node 454 can communicate the information from the received signals 456 to an actuator 458 (e.g., implanted actuator; stimulator unit 120; actuator 310) of the actuating assembly 404.

As schematically illustrated by FIG. 4B, in certain embodiments, the monitoring circuitry 420 comprises one or more circuits configured to monitor the operation of the auditory prosthesis 100, 200, 300 for indications that the filtering being applied by the filtering circuitry 440 and the signal processing circuitry 410 may be degrading the acoustic response of the auditory prosthesis by generating unwanted acoustic effects (e.g., artifacts, noise, oscillations, and/or instabilities). For example, the monitoring circuitry 420 can comprise one or more of: a telemetry monitor circuit 460 configured to monitor the at least one communication channel 414; a power/current monitor circuit 470 configured to monitor a power and/or current being consumed at the first node 452; a data signal monitor circuit 480 configured to monitor the signal processing circuitry 410 and/or the processed data signals 412. While FIG. 4B schematically illustrates example monitoring circuitry 420 comprising each of the telemetry monitor circuit 460, the power/current monitor circuit 470, and the data signal monitor circuit 480, in certain other embodiments, as described more fully below, the monitoring circuitry 420 comprises only one or two of the telemetry monitor circuit 460, the power/current monitor circuit 470, and the data signal monitor circuit 480.

Figure 5A:
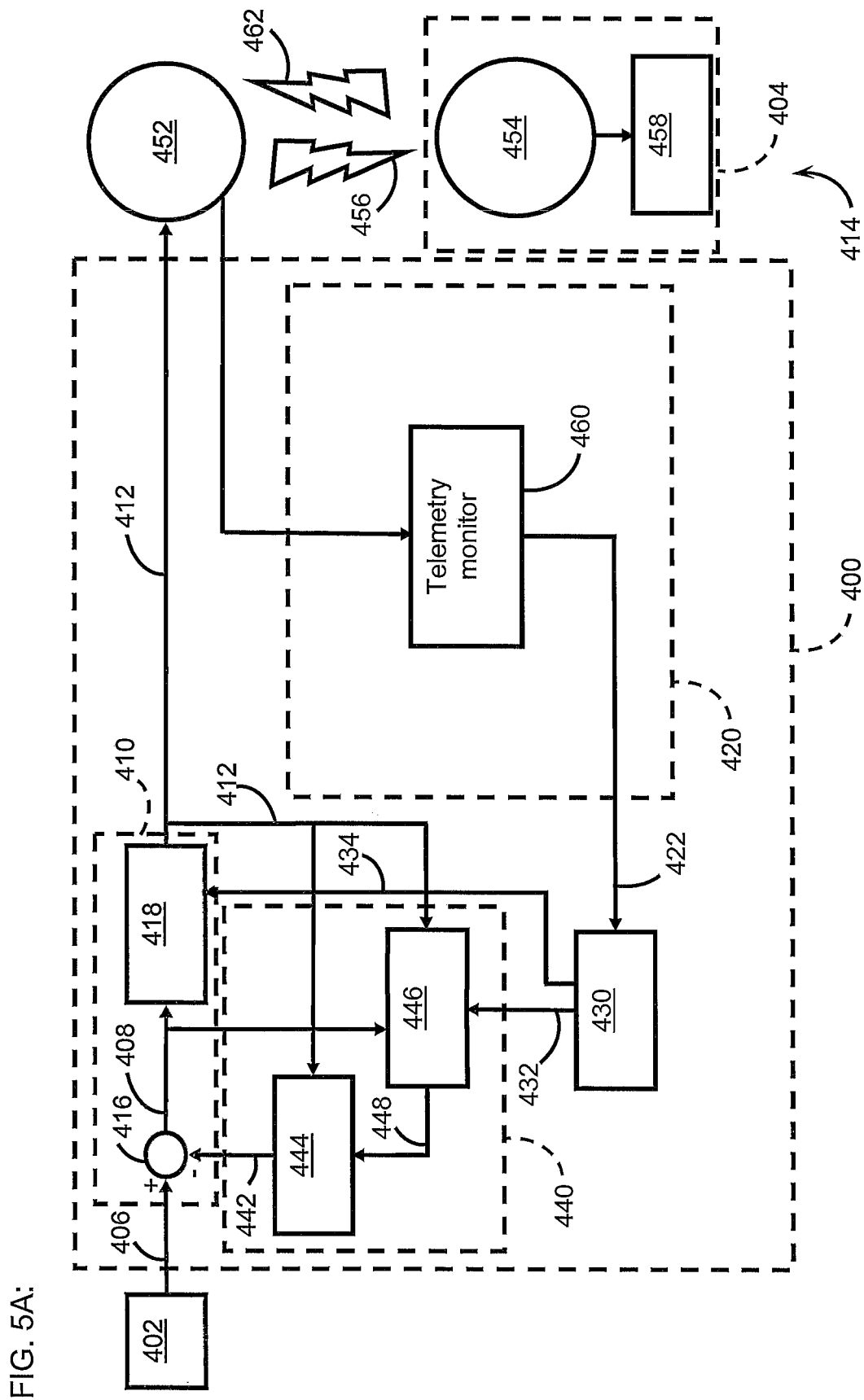
FIG. 5A schematically illustrates an example apparatus comprising a telemetry monitor circuit in accordance with certain embodiments described herein.

FIG. 5A schematically illustrates an example apparatus 400 comprising a telemetry monitor circuit 460 in accordance with certain embodiments described herein. The example apparatus 400 can be used in conjunction with auditory prostheses that are fully implantable, totally implantable, mostly implantable, partially implantable, or semi-implantable. The first node 452 is configured to transmit the signals 456 (e.g., RF link wireless signals; inductive wireless signals) indicative of the processed data signals 412 to the second node 454, which is configured to provide the information from the received signals 456 to the actuator of the actuating assembly 404. In addition, the second node 454 is configured to transmit telemetry signals 462 (e.g., RF backlink signals) and the first node 452 is configured to receive the telemetry signals 462 from the second node 452. For example, the telemetry signals 462 can be transmitted by the second node 452 at regular intervals (e.g., intervals less than one second, less than 500 milliseconds, less than 100 milliseconds). In certain embodiments, the telemetry signals 462 are encoded with information identifying the actuating assembly 404 from which the telemetry signals 462 are transmitted.

The telemetry monitor circuit 460 is configured to monitor the status of the wireless link between the apparatus 400 and the actuating assembly 404 by detecting whether the first node 452 is receiving the telemetry signals 462. For example, the telemetry monitor circuit 460 can be configured to interpret the received telemetry signals 462 by the first node 452 as being indicative of an operative wireless communication link between the apparatus 400 and the actuating assembly 404 (e.g., between the first node 452 and the second node 454) and to interpret the absence of received telemetry signals 462 by the first node 452 as being indicative of a non-operative wireless communication link between the apparatus 400 and the actuating assembly 404. In certain embodiments in which the telemetry signals 462 are encoded with information identifying the actuating assembly 404 from which the telemetry signals 462 are transmitted, the telemetry monitor circuit 460 is configured to decode the information from the received telemetry signals 462 and to compare the information to previously stored information data (e.g., from a storage device of the apparatus 400) indicative of the actuating assembly 404 expected to be operatively coupled to the apparatus 400. For example, the telemetry monitor circuit 460 can be configured to interpret a match (e.g., good implant identification) between the information received from the telemetry signals 462 and the previously-stored identification data as being indicative of an operative wireless communication link between the apparatus 400 and the expected (e.g., correct) actuating assembly 404 and to interpret a non-match (e.g., bad implant identification) between the information received from the telemetry signals 462 and the previously-stored identification data as being indicative of an operative wireless communication link between the apparatus 400 and a non-expected (e.g., incorrect) actuating assembly 404 (e.g., an actuating assembly 404 implanted in another ear of the recipient having an actuating assembly 404 on each ear).

In certain embodiments, the telemetry monitor circuit 460 is further configured to generate the monitoring signals 422 indicative of the detected status of the wireless link between the apparatus 400 and the actuating assembly 404 and to transmit the monitoring signals 422 to the control circuitry 430. For example, upon the telemetry monitor circuit 460 not detecting the telemetry signals 462, the monitoring signals 422 are indicative of a non-operative wireless communication link between the apparatus 400 and the actuating assembly 404, and upon the telemetry monitor circuit 460 detecting the telemetry signals 462, the monitoring signals 422 are indicative of an operative wireless communication link between the apparatus 400 and the actuating assembly 404. For another example, upon the telemetry monitor circuit 460 detecting telemetry signals 462 encoded with information not matching the previously-stored identification data indicative of the expected actuating assembly 404, the monitoring signals 422 are indicative of an improper wireless communication link, and upon the telemetry monitor circuit 460 detecting telemetry signals 462 encoded with information matching the previously-stored identification data indicative of the expected actuating assembly 404, the monitoring signals 422 are indicative of a proper wireless communication link. In certain embodiments, the telemetry monitor circuit 460 is configured to utilize load-shift-keying (LSK) for back telemetry.

Figure 5B:
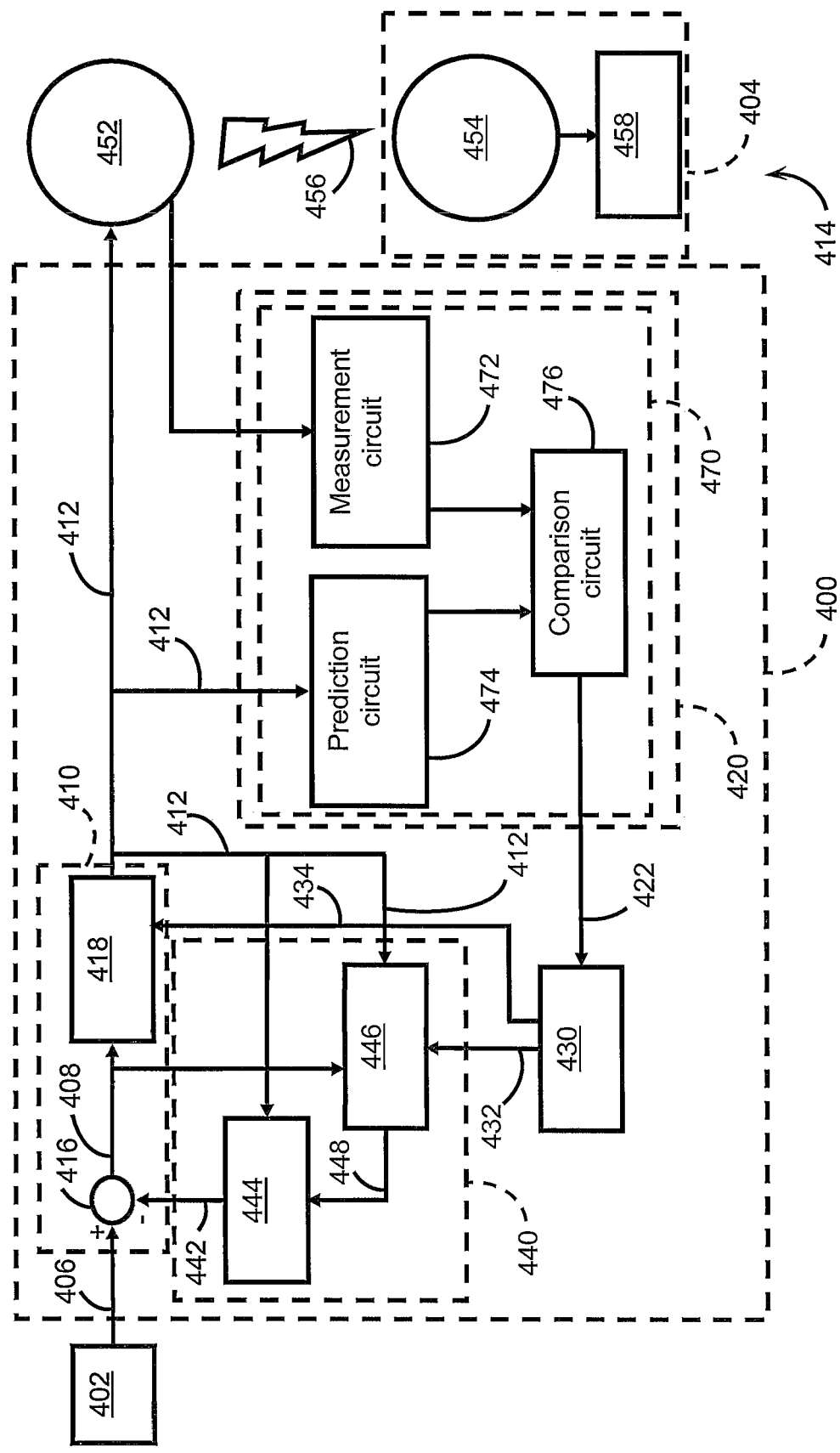
FIGS. 5B and 5C schematically illustrate two example apparatuses comprising a power/current monitor circuit in accordance with certain embodiments described herein.
Figure 5C:
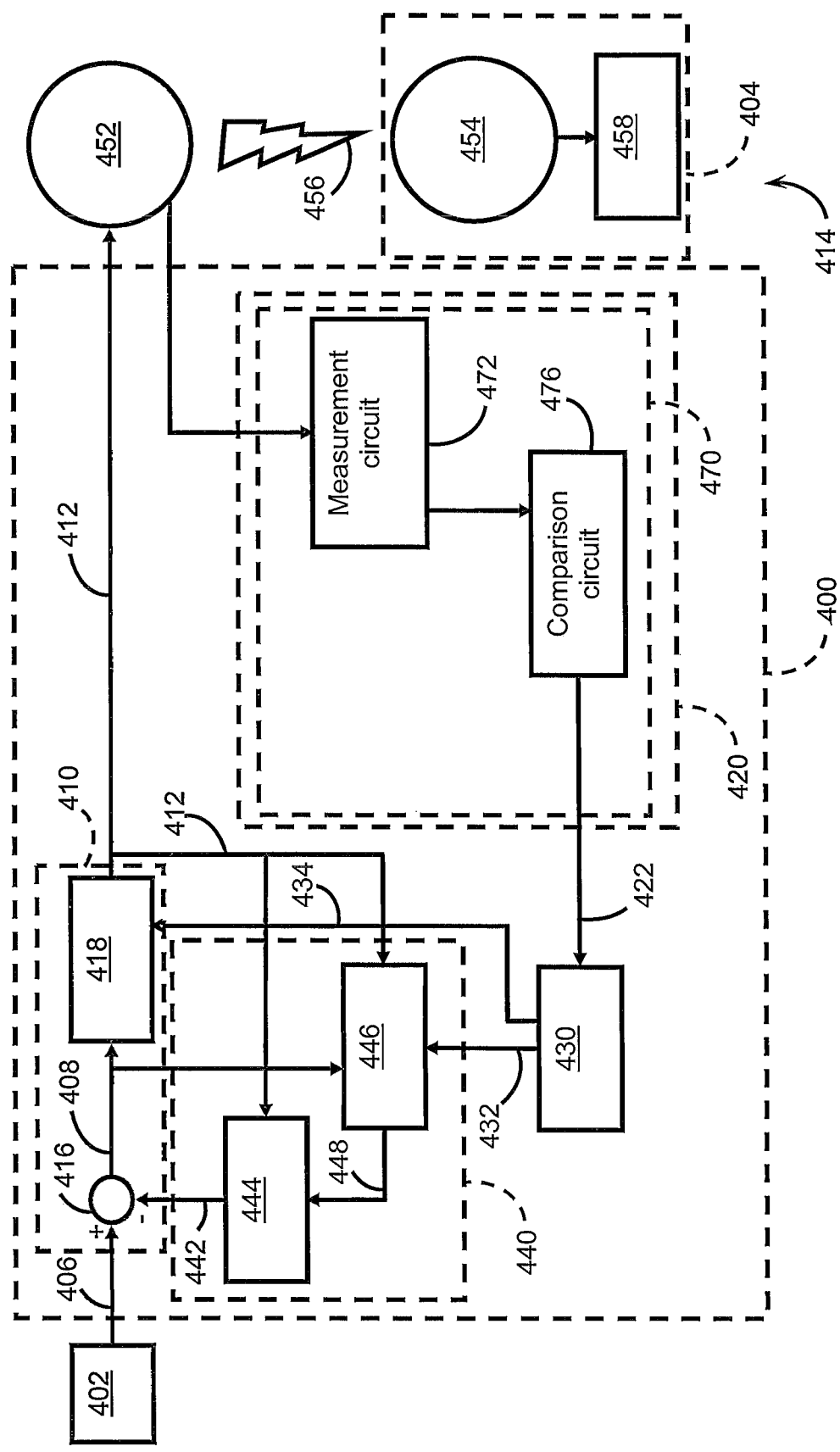

FIGS. 5B and 5C schematically illustrate two example apparatuses 400 comprising a power/current monitor circuit 470 in accordance with certain embodiments described herein. The example apparatuses 400 can be used in conjunction with auditory prostheses that are fully implantable, totally implantable, mostly implantable, partially implantable, or semi-implantable. The power/current monitor circuit 470 is configured to utilize the dependence of the power/ current consumed by the first node 452 on the successful wireless transmission of the signals 456 from the first node 452 to the second node 454 of the actuating assembly 404.

As schematically illustrated by FIG. 5B, the power/current monitor circuit 470 comprises a measurement circuit 472 operatively coupled to the first node 452 and configured to measure the power/current being consumed by the first node 452. The power/current monitor circuit 470 further comprises a prediction circuit 474 configured to monitor the signal processing circuitry 410 and/or the processed data signals 412 from the signal processing circuitry 410 and to predict the power/current expected to be consumed by the first node 452 while successfully wirelessly transmitting the signals 456 to the second node 454 (e.g., based on a model of the auditory prosthesis system). The power/current monitor circuit 470 further comprises a comparison circuit 476 operatively coupled to the measurement circuit 472 and the prediction circuit 474. The comparison circuit 476 is configured to compare the measured power/current consumed by the first node 452 with the power/current predicted to be consumed by the first node 452.

The power/current monitor circuit 470 is configured to monitor the status of the wireless link between the apparatus 400 and the actuating assembly 404 by detecting whether the first node 452 is consuming an expected level of power/current that is indicative of successful wireless transmission of the signals 456 to the actuating assembly 404. For example, the comparison circuit 476 can be configured to interpret a match (e.g., within a predetermined range) between the measured power/current being consumed by the first node 452 from the measurement circuit 472 and the predicted power/current from the prediction circuit 474 as being indicative of an operative wireless communication link between the apparatus 400 and the actuating assembly 404 (e.g., between the first node 452 and the second node 454) and to interpret a non-match (e.g., outside the predetermined range) between the measured power/current being consumed by the first node 452 from the measurement circuit 472 and the predicted power/current from the prediction circuit 474 as being indicative of a non-operative wireless communication link between the apparatus 400 and the actuating assembly 404.

In certain other embodiments, the power/current monitor circuit 470 comprises the measurement circuit 472 and the comparison circuit 476 operatively coupled to the measurement circuit 472 (e.g., without the prediction circuit 474), as schematically illustrated by FIG. 5C. For example, the comparison circuit 476 can be configured to compare the measured power/current being consumed by the first node 452 from the measurement circuit 472 to a previously-stored power/current level (e.g., from a storage device of the apparatus 400). The comparison circuit 476 can interpret a measured power/current greater than or equal to the previously-stored power/current level as being indicative of an operative wireless communication link between the apparatus 400 and the actuating assembly 404 (e.g., between the first node 452 and the second node 454) and to interpret a measured power/current less than the previously-stored power/current level as being indicative of a non-operative wireless communication link between the apparatus 400 and the actuating assembly 404.

In certain embodiments, the power/current monitor circuit 470 is further configured to generate the monitoring signals 422 indicative of the detected status of the wireless link between the apparatus 400 and the actuating assembly 404 and to transmit the monitoring signals 422 to the control circuitry 430. For example, upon the power/current monitor circuit 470 detecting a non-match (e.g., outside the predetermined range) between the measured power/current being consumed by the first node 452 from the measurement circuit 472 and the predicted power/current from the prediction circuit 474, the monitoring signals 422 are indicative of a non-operative wireless communication link between the apparatus 400 and the actuating assembly 404, and upon the power/current monitor circuit 470 detecting a match (e.g., within the predetermined range) between the measured power/current being consumed by the first node 452 from the measurement circuit 472 and the predicted power/current from the prediction circuit 474, the monitoring signals 422 are indicative of an operative wireless communication link between the apparatus 400 and the actuating assembly 404. For another example, upon the power/current monitor circuit 470 detecting that the measured power/current is less than the previously-stored power/current level, the monitoring signals 422 are indicative of a non-operative wireless communication link, and upon the power/current monitor circuit 470 detecting that the measured power/current is greater than or equal to the previously-stored power/current level, the monitoring signals 422 are indicative of a proper wireless communication link.

Figure 5D:
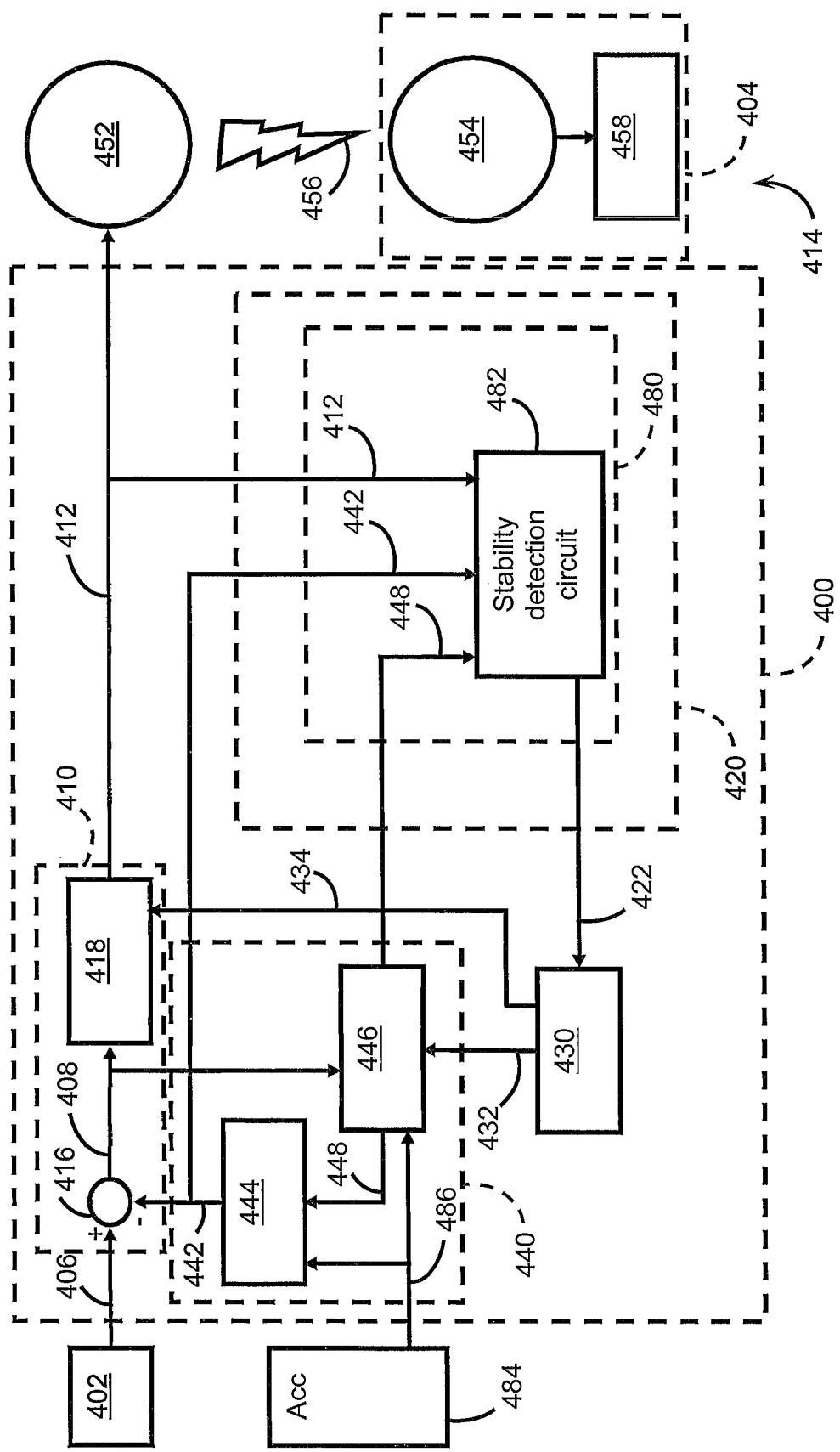
FIG. 5D schematically illustrates an example apparatus comprising a data signal monitor circuit in accordance with certain embodiments described herein.

FIG. 5D schematically illustrates an example apparatus 400 comprising a data signal monitor circuit 480 in accordance with certain embodiments described herein. The example apparatus 400 of FIG. 5D can be used in conjunction with auditory prostheses that include an implantable microphone assembly (e.g., fully implantable, totally implantable, or mostly implantable auditory prostheses) that comprises the at least one acoustic transducer 402 and at least one accelerometer 484. In certain embodiments in which the apparatus 400 is used in conjunction with a fully or totally implantable auditory prosthesis, the link between the first node 452 and the second node 454 by which the signals 456 are transmitted comprises a wired link (e.g., a direct wired connection between the apparatus 400 and the actuator 404). In certain other embodiments, the link between the first node 452 and the second node 454 by which the signals 456 are transmitted comprises a wireless link (e.g., an RF link; an inductive link) between the apparatus 400 and the actuator 404.

The at least one accelerometer 484 is configured to respond to vibrations received from a source that is internal to the recipient (e.g., feedback from an implanted actuator; biological noise) by generating accelerometer signals 486 indicative of the vibrations and providing the accelerometer signals 486 to the filtering circuitry 440 (e.g., to filter circuit 444 and a filter update circuit 446 as shown in FIG. 5D) of the apparatus 400. The filtering circuitry 440 is configured to use the accelerometer signals 486 (e.g., averaging the accelerometer signals 486 over an integration time period) in determining the filter coefficient values 448 to be used in generating the filtering signals 442 to be subtracted out from the acoustic transducer signals 406 (e.g., at the adder 416), thereby generating the resultant signals 408 provided to the AGC 418 of the signal processing circuitry 410.

In certain embodiments, the stability detection circuit 482 is configured to receive one or more of the following: processed data signals 412 from the signal processing circuitry 410; filtering signals 442 received from the filtering circuitry 440; filter coefficient values 448 received from the filtering circuitry 440. The stability detection circuit 482 uses the received information to detect a status of the signal processing circuitry 410 and/or the filtering circuitry 440. The detected status can include incoherent behavior (e.g., instabilities or other aberrations) of the signal processing circuitry 410 and/or the filtering circuitry 440 (e.g., excessive cancellation due to impulse noise or the recipient's own voice detected by the acoustic transducer 402).

For example, the stability detection circuit 482 can be configured to receive the processed data signals 412 from the signal processing circuitry 410 and to use the received information to determine whether the signal processing circuitry 410 is unstable (e.g., evidenced by the processed data signals 412 having artifacts, noise, oscillations, and/or instabilities), whether the signal processing circuitry 410 is using signal processing parameters that are outside one or more predetermined parameter ranges (e.g., parameter ranges stored in a storage device of the data signal monitor circuit 480), whether the processed data signals 412 have attributes outside one or more predetermined attribute ranges (e.g., attribute ranges stored in a storage device of the data signal monitor circuit 480), and/or how long the attributes of the processed data signals 412 and/or the signal processing parameters have been outside their predetermined ranges.

For another example, the stability detection circuit 482 can be configured to receive the filtering signals 442 and/or the filter coefficient values 448 from the filter update circuit 446 and to use the received information to determine whether the filtering circuitry 440 is unstable (e.g., evidenced by the filtering signals 442 having artifacts, noise, oscillations, and/or instabilities, whether the filter coefficient values 448 are outside one or more predetermined coefficient value ranges (e.g., coefficient value ranges stored in a storage device of the data signal monitor circuit 480), whether the filtering signals 442 have attributes outside one or more predetermined attribute ranges (e.g., attribute ranges stored in a storage device of the data signal monitor circuit 480), and/or how long the attributes of the filtering signals 442 and/or the filter coefficient values 448 have been outside their predetermined ranges.

The stability detection circuit 482 is further configured to generate the monitoring signals 422 indicative of the detected status of the signal processing circuitry 410 and/or the filtering circuitry 440 (e.g., whether an error condition exists), and to transmit the monitoring signals 422 to the control circuitry 430. For example, the error condition can comprise one or more of the following error conditions: instability of the signal processing circuitry 410; the signal processing circuitry 410 using signal processing parameters that are outside one or more predetermined parameter ranges; the processed data signals 412 having attributes outside one or more predetermined attribute ranges. One or more of these error conditions can be due to the absence of a communication channel 414 that is operative (e.g., a communication channel successfully transmitting signals 456 from the apparatus 400 to an actuating assembly 404) and proper (e.g., the signals 456 transmitted to the correct actuating assembly 404).

In certain embodiments, as schematically illustrated by FIGS. 4A-4B and 5A-5D, the control circuitry 430 is configured to respond to the monitoring signals 422 received from the monitoring circuitry 420 (e.g., from one or more of the telemetry monitor circuit 460, power/current monitory circuit 470, and the data signal monitor circuit 480) by generating the filtering control signals 432 transmitted to the filtering circuitry 440. For example, in response to the monitoring signals 422 being indicative of an error condition, the filtering control signals 432 can be configured to command the filtering circuitry 440 to mitigate (e.g., avoid; reduce; inhibit; cancel) acoustic effects (e.g., artifacts, noise, oscillations, and/or instabilities) in the filtering signals 442 due to the error condition by modifying its operational state (e.g., commanding the filtering circuitry 440 to reset, to stop the filtering, to slow the speed of the filtering being applied, to change the type of filtering being applied, and/or to enter a safe operational mode) and/or modifying the filter coefficient values being utilize by the filtering circuitry 440 to generate the filtering signals 442 (e.g.; commanding the filtering circuitry 440 to utilize a predetermined set of filter coefficient values corresponding to safe operation, the predetermined set of filter coefficient values communicated to the filtering circuitry 440 by a storage device in operable communication with the filtering circuitry 440). The storage device can be configured to receive and store filter coefficient values from the filtering circuitry 440 at intervals during a normal operational mode, and to communicate the stored filter coefficient values to the filtering circuitry 440 when the filtering circuitry 440 enters a safe operational mode.

In certain embodiments, as schematically illustrated by FIGS. 5A-5D, the control circuitry 430 is further configured to respond to the monitoring signals 422 received from the monitoring circuitry 420 (e.g., from one or more of the telemetry monitor circuit 460, power/current monitory circuit 470, and the data signal monitor circuit 480) by generating processing control signals 434 transmitted to the signal processing circuitry 410. In response to the monitoring signals 422 being indicative of an error condition, the control circuitry 430 generates processing control signals 434 and transmits the processing control signals 434 to the signal processing circuitry 410 (e.g., the AGC 418). The signal processing circuitry 410 (e.g., the AGC 418) is configured to respond to the processing control signals 434 by mitigating (e.g., avoiding; reducing; inhibiting; canceling) the error condition. For example, the signal processing circuitry 410 can apply modifications to maintain the signal processing in a stable and controlled state (e.g., by reducing the gain of the signal processing; changing a compression of the signal processing).

Figure 6:
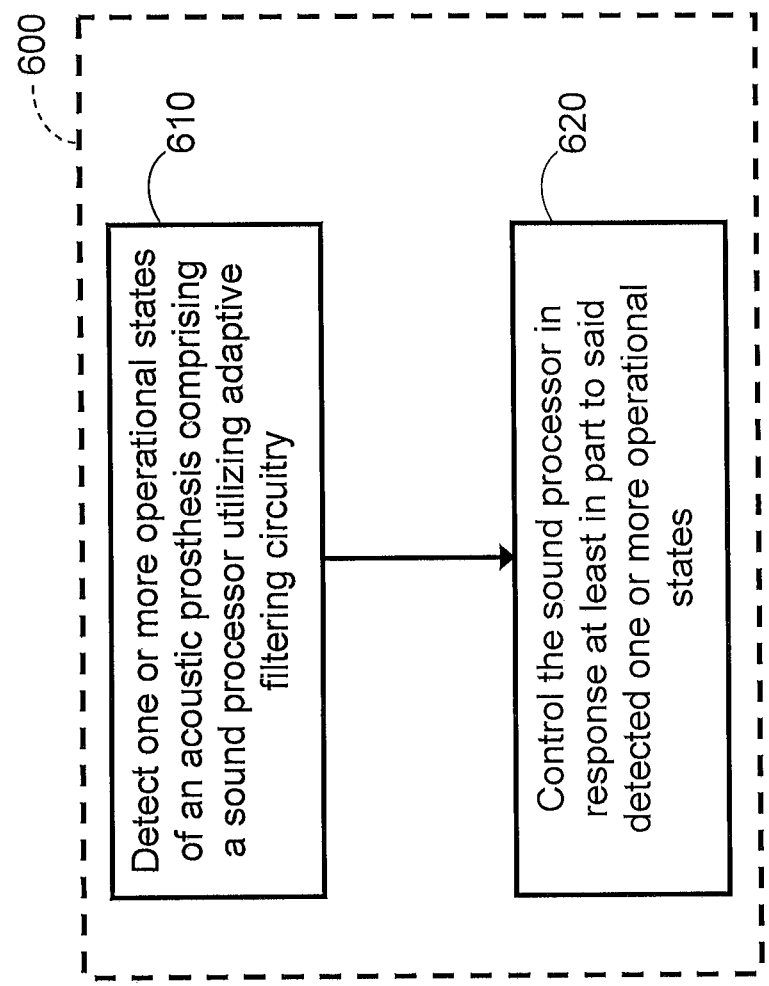
FIG. 6 is a flow diagram of an example method in accordance with certain embodiments described herein.

FIG. 6 is a flow diagram of an example method 600 in accordance with certain embodiments described herein. While the method 600 is described herein by referring to the example acoustic prostheses 100, 200, 300 of FIGS. 1, 2A-2B, and 3 and to the example apparatuses 400 of FIGS. 4A-4B and 5A-5D, other acoustic prostheses and other apparatuses are also compatible with being used with the method 600 in accordance with certain embodiments described herein. For example, the auditory prosthesis can include a cochlear implant device, middle ear implant device, bone conduction device (e.g., active bone conduction device; passive bone conduction device, percutaneous bone conduction device; transcutaneous bone conduction device), Direct Acoustic Cochlear Implant (DACI), middle ear transducer (MET), electro-acoustic implant device, other types of auditory prosthesis device, and/or combinations or variations thereof. The apparatus 400 can comprise a sound processor that is implanted on or within the recipient or that is external to the recipient.

In an operational block 610, the method comprises detecting one or more operational states of an auditory prosthesis implanted on or within a recipient. The auditory prosthesis (e.g., auditory prosthesis 100, 200, 300) comprises a sound processor (e.g., apparatus 400) utilizing adaptive filtering circuitry to improve an acoustic response of the auditory prosthesis 100, 200, 300. In an operational block 620, the method further comprises controlling the sound processor in response at least in part to said detected one or more operational states. As described more fully herein, the detected one or more operational states can be unwanted operational states in which the auditory prosthesis exhibits conditions which are prone to generating unwanted acoustic effects (e.g., acoustic effects which cause discomfort to the recipient, such as artifacts, noise, oscillations, and/or instabilities).

In certain embodiments, the one or more operational states comprises an absence of a communication link 414 (e.g., a wireless communication link or a wired communication link) between the sound processor (e.g., apparatus 400) and an implanted portion (e.g., an implanted actuating assembly 404 comprising at least one actuator 458 in operative communication with at least a portion of the auditory system of the recipient; stimulator unit 120; actuator 310) of the auditory prosthesis 100, 200, 300. For example, the communication link 414 can comprise wireless communications between a first node 452 (e.g., first radio-frequency antenna; first coil) of the sound processor and a second node 454 (e.g., second radio-frequency antenna; second coil in inductive communication with the first coil) of the actuating-assembly 404.

In certain embodiments, detecting the absence of a wireless communication link 414 comprises detecting an absence of a telemetry signal 462 from the actuating assembly 404 (e.g., using a telemetry monitor circuit 460 of the apparatus 400 in operative communication with the first node 452). For example, as shown by FIG. 5A, the telemetry monitor circuit 460 can interpret telemetry signals 462 received by the first node 452 as being indicative of an operative wireless communication link 414 and can interpret the absence of telemetry signals 462 received by the first node 452 as being indicative of a non-operative wireless communication link 414. In certain embodiments in which the telemetry signals 462 are encoded with information identifying the actuating assembly 404 from which the telemetry signals 462 are transmitted, the telemetry monitor circuit 460 decodes the information from the received telemetry signals 462 and compares the information to previously-stored information data (e.g., from a storage device of the apparatus 400) indicative of the actuating assembly 404 expected to be operatively coupled to the apparatus 400. For example, a match between the information received from the telemetry signals 462 and the previously-stored identification data can be indicative of an operative wireless communication link 414 between the apparatus 400 and the expected actuating assembly 404 (e.g., a proper wireless communication link 414) and a non-match between the information received from the telemetry signals 462 and the previously-stored identification data can be indicative of an operative wireless communication link 414 between the apparatus 400 and a non-expected actuating assembly 404 (e.g., an improper wireless communication link 414 to an actuating assembly 404 implanted in another ear of the recipient).

In certain embodiments, detecting the absence of a wireless communication link 414 can comprise detecting consumption by the first node 452 of at least one of an electric current and an electric power. For example, as shown by FIG. 5C, the detected consumption by the first node 452 can be compared to at least one predetermined consumption level (e.g., previously stored on a storage device of the apparatus 400), and detecting the absence of the wireless communication link 414 can comprise determining that the detected consumption is less than a predetermined lower-bound consumption level (e.g., the detected consumption is too low) or determining that the detected consumption is greater than a predetermined upper-bound consumption level (e.g., the detected consumption is too high). For another example, as shown by FIG. 5B, the detected consumption by the first node 452 can be compared to an estimated consumption level (e.g., estimated by a prediction circuit 474 of the apparatus 400 based on the output of the signal processing circuitry 410), and detecting the absence of the wireless communication link 414 can comprise determining that the detected consumption is less than the estimated consumption level (e.g., the detected consumption is too low) or is greater than the estimated consumption level (e.g., the detected consumption is too high), within a predetermined range (e.g., ±10%; ±5%; ±2%).

In certain embodiments, the one or more operational states comprises a failure of the adaptive filtering circuitry (e.g., filtering circuitry 440) to determine a set of filter coefficient values after a predetermined number of activity cycles. For example, the stability detection circuit 482 can monitor the set of filter coefficient values 448 generated by the filter update circuit 446 of the filtering circuitry 440 and can monitor the number of activity cycles performed by the filter update circuit 446. Detecting the failure can comprise determining that the filter coefficient values 448 are varying (e.g., oscillating) by more than a predetermined amount (e.g., previously stored on the storage device of the apparatus 400) after a predetermined number (e.g., previously stored on the storage device of the apparatus 400) of activity cycles.

In certain embodiments, the one or more operational states comprises the set of filter coefficient values determined by the adaptive filtering circuitry (e.g., filtering circuitry 440) being outside a predetermined range of coefficient values. For example, as shown in FIG. 5D, the stability detection circuit 482 can monitor the set of filter coefficient values 448 generated by the filter update circuit 446 of the filtering circuitry 440 and detecting the absence of the communication link 414 can comprise determining that the filter coefficient values 448 are outside the predetermined range of coefficient values (e.g., previously stored on the storage device of the apparatus 400).

In certain embodiments, the one or more operational states comprises an instability of data signals (e.g., the processed data signals 412) outputted from the sound processor (e.g., from the signal processing circuitry 410) and transmitted to the implanted portion of the auditory prosthesis (e.g., actuating assembly 404). For example, as shown in FIG. 5D, the stability detection circuit 482 can be configured to monitor the processed data signals 412 from the signal processing circuitry 410 and to determine whether the processed data signals 412 include one or more instabilities that degrade an acoustic response of the auditory prosthesis. Such instabilities can include but are not limited to: one or more artifacts, oscillations, attributes (e.g., magnitudes; temporal profiles) that are outside one or more predetermined attribute ranges (e.g., attribute ranges stored in a storage device of the apparatus 400), and/or attributes that are outside their predetermined attribute ranges for a time period longer than a predetermined time period.

In certain embodiments, the one or more operational states comprises an instability of filtering signals (e.g., the filtering signals 442) generated by the adaptive filtering circuitry (e.g., the filtering circuitry 440). For example, as shown in FIG. 5D, the stability detection circuit 482 can be configured to monitor the filtering signals 442 from the filter update circuit 446 and to determine whether the filtering signals 442 include one or more instabilities that degrade an acoustic response of the auditory prosthesis. Such instabilities can include but are not limited to: one or more artifacts, oscillations, attributes (e.g., magnitudes; temporal profiles)

that are outside one or more predetermined attribute ranges (e.g., attribute ranges stored in a storage device of the apparatus 400), and/or attributes that are outside their predetermined attribute ranges for a time period longer than a predetermined time period.

In certain embodiments, controlling the sound processor in response at least in part to said detected one or more operational states comprises operating the sound processor to mitigate (e.g., avoid; reduce; inhibit; cancel) discomfort to the recipient (e.g., due to unwanted artifacts, noise, oscillations, and/or instabilities caused by the adaptive filtering circuitry). The modified operation of the sound processor in response to the detected one or more operational states is performed for a predetermined period of time (e.g., a period of time stored in a storage device of the apparatus 400) or until the one or more operational states which triggered the modified operation of the adaptive filtering circuitry is no longer detected. In certain embodiments, the particular actions performed to control the sound processor can depend on the particular detected operational state of the auditory prosthesis or on the length of time during which the detected operational state exists (e.g., whether the communication link is non-operational for a time period less than a predetermined time period or for a time period greater than the predetermined time period).

For example, controlling the sound processor can comprise changing an operational mode of the adaptive filtering circuitry (e.g., temporarily changing from a first filtering scheme to a second filtering scheme less prone to generating unwanted artifacts, noise, oscillations, and/or instabilities than is the first filtering scheme). For another example, controlling the sound processor can comprise halting operation of the adaptive filtering circuitry (e.g., temporarily stopping, turning off, or pausing the filtering circuitry 440 while continuing to use the signal processing circuitry 410 to generate processed data signals 412). For still another example, controlling the sound processor can comprise reducing an operation speed of the adaptive filtering circuitry (e.g., temporarily slowing the adaptation speed of the filtering circuitry 440; temporarily increasing an integration time period over which the filtering circuitry 440 averages the accelerometer signals 486).

For yet another example, controlling the sound processor can comprise changing values of one or more filter coefficients of the adaptive filtering circuitry and/or changing values of one or more coefficients (e.g., band gains of the signal processing circuitry 410) used by the sound processor. In certain embodiments, the values can be changed to one or more predetermined values (e.g., values that are stored in a storage device of the apparatus 400; values that are known or expected to provide stable performance of the auditory prosthesis; values that were predetermined at the time of fitting the auditory prosthesis to the recipient and known or expected to result in acceptable performance without undesirable feedback). In certain embodiments in which the recipient has multiple auditory prosthesis sub-systems (e.g., bilateral recipients having a first auditory prosthesis sub-system corresponding to a first ear of the recipient and a second auditory prosthesis sub-system corresponding to a second ear of the recipient), the filter coefficient values obtained from the adaptive filtering circuitry of one auditory prosthesis sub-system can be used by the adaptive filtering circuitry of the other auditory prosthesis sub-system. For example, when an ipsilateral auditory prosthesis is in a bilateral mode, the storage device can be configured to receive and store filter coefficient values from the filtering circuitry of a contralateral auditory prosthesis and, in a safe operational mode of the ipsilateral auditory prosthesis, to communicate the stored filter coefficient values to the filtering circuitry of the ipsilateral auditory prosthesis.

For example, for bilateral symmetric systems in which both auditory prosthesis sub-systems are of the same type (e.g., both are cochlear implant devices or both are middle ear implant devices), if one of the unwanted operational states is detected for the first auditory prosthesis sub-system, the filter coefficient values from the second auditory prosthesis sub-system can be used directly by the first auditory prosthesis sub-system. For bilateral bimodal systems in which the two auditory prosthesis sub-systems are of different types (e.g., one is a cochlear implant device and the other is a middle ear implant device; or one is an implanted device and the other is an external device, such as a hearing aid), if one of the unwanted operational states is detected for the first auditory prosthesis sub-system, the filter coefficient values from the second auditory prosthesis sub-system can be used by the first auditory prosthesis sub-system (e.g., after converting the values to be appropriate for the differing type of auditory prosthesis). The communications between the two auditory prosthesis sub-systems can utilize one or more wireless communication links and/or one or more wired communication links (e.g., as described by U.S. Pat. Nos. 9,020,169 and 9,042,996). Certain such embodiments advantageously provide a useful coordination between the hearing systems on both ears, whether these hearing systems are similar to one another or different from one another.

In certain embodiments, controlling the sound processor comprises changing an operational mode of the auditory prosthesis. For example, upon the detection of one or more unwanted operational states, the sound processor (e.g., apparatus 400) can be temporarily placed in a safe mode in which it does not utilize the adaptive filtering circuitry (e.g., filtering circuitry 440), or temporarily placed in a sleep mode in which it is not utilize to generate and transmit data signals to the actuating assembly. For another example, upon the detection of one or more unwanted operational states, the adaptation mode of the adaptive filtering circuitry (e.g., apparatus 400) can be changed (e.g., from a normalized mode to a signed or fixed-step mode), or the adaptive filtering circuitry can be cleared or reset.

For still another example, the auditory prosthesis can comprise a first microphone and a second microphone, both configured to transmit microphone signals to the sound processor (e.g., apparatus 400). When the one or more operational states is detected during an operational mode of the auditory prosthesis in which the sound processor is using the microphone signals from one of the microphones, the operational mode of the auditory prosthesis can be temporarily changed to a different operational mode in which the sound processor uses the microphone signals from the other microphone. In certain embodiments, the first microphone is implanted on or within the recipient and the second microphone is external to the recipient, while in certain other embodiments, the first microphone is external to the recipient and the second microphone is implanted on or within the recipient. In certain embodiments, the first microphone is part of a first auditory prosthesis sub-system corresponding to a first ear of the recipient, and the second microphone is part of a second auditory prosthesis sub-system corresponding to a second ear of the recipient. Certain such embodiments advantageously allow the auditory prosthesis, upon detection of an unwanted operational state, to switch the audio source automatically, between implanted and external microphone and/or between microphone on different ears of the recipient.

Figure 7:
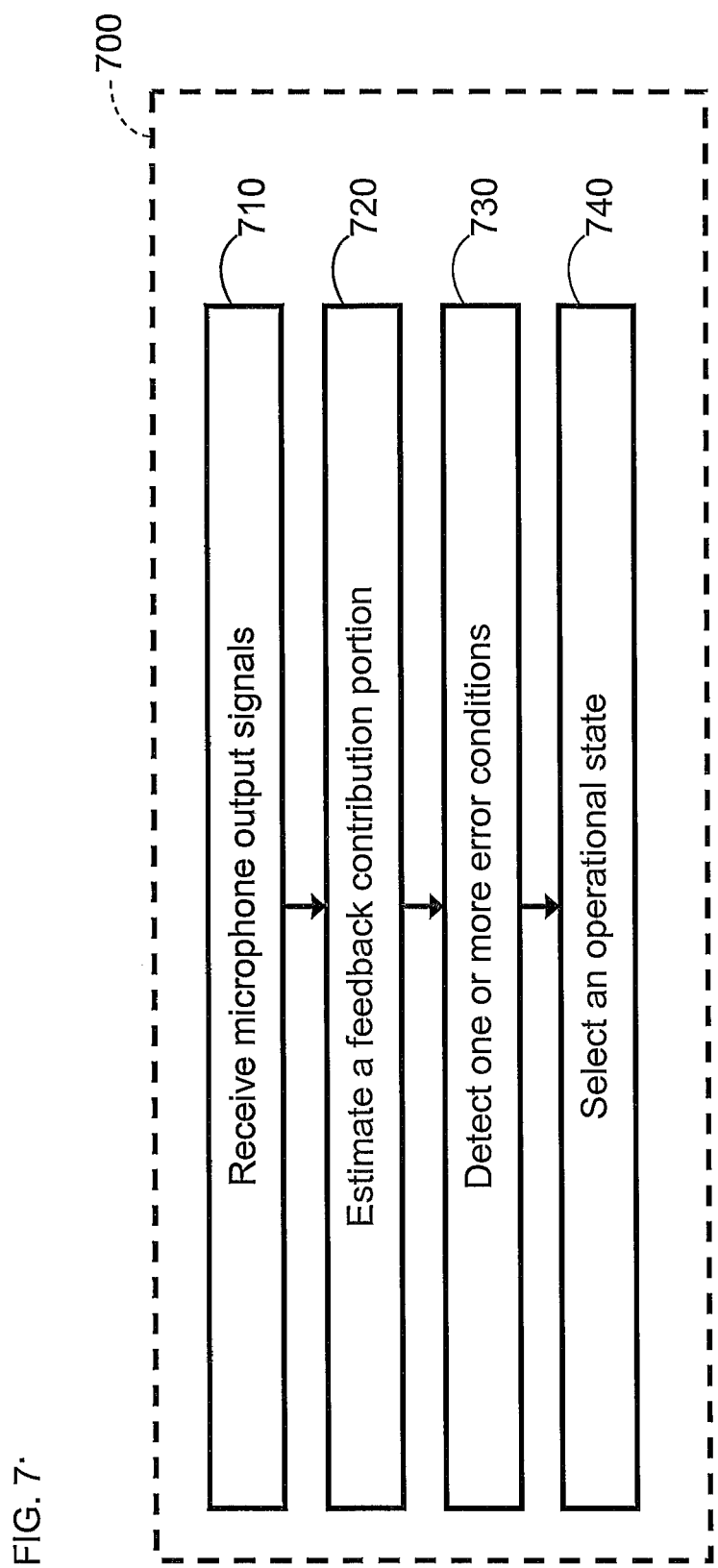
FIG. 7 is a flow diagram of an example method performed by at least one sound processor of an auditory prosthesis in accordance with certain embodiments described herein.

FIG. 7 is a flow diagram of an example method 700 performed by at least one sound processor (e.g., apparatus 400) of an auditory prosthesis in accordance with certain embodiments described herein. While the method 700 is described herein by referring to the example acoustic prostheses 100, 200, 300 of FIGS. 1, 2A-2B, and 3 and to the example apparatuses 400 of FIGS. 4A-4B and 5A-5D, other acoustic prostheses and other apparatuses are also compatible with being used with the method 700 in accordance with certain embodiments described herein. For example, the auditory prosthesis can include a cochlear implant device, middle ear implant device, bone conduction device (e.g., active bone conduction device; passive bone conduction device, percutaneous bone conduction device; transcutaneous bone conduction device), Direct Acoustic Cochlear Implant (DACI), middle ear transducer (MET), an electroacoustic implant device, other types of auditory prosthesis device, and/or combinations or variations thereof. The at least one sound processor can be implanted on or within the recipient or can be external to the recipient.

In an operational block 710, the method 700 comprises receiving microphone output signals (e.g., transducer signals 406) from at least one microphone assembly (e.g., at least one acoustic transducer 402) of the auditory prosthesis. The microphone output signals are indicative of sound received by the at least one microphone assembly. In an operational block 720, the method 700 further comprises estimating a feedback contribution portion of the microphone output signals. In an operational block 730, the method 700 further comprises detecting one or more error conditions indicative of errors in the estimated feedback contribution portion. In an operational block 740, the method 700 further comprises selecting an operational state of the at least one sound processor in response to the detected one or more error conditions.

In certain embodiments, the at least one sound processor comprises an active feedback canceler (e.g., filtering circuitry 440) configured to estimate the feedback contribution portion of the microphone output signals and to generate estimation signals (e.g., filtering signals 442) indicative of the estimated feedback contribution portion of the microphone output signals. For example, the active feedback canceler can be configured to receive accelerometer signals 486 from at least one accelerometer 484 of an implanted microphone assembly and to estimate the feedback contribution portion based at least in part on the accelerometer signals 486.

In certain embodiments, the at least one sound processor further comprises an adjustable gain controller 418 (e.g., part of the signal processing circuitry 410) configured to generate output signals (e.g., data signals 412) in response at least in part to the microphone output signals and the estimation signals. The output signals are indicative of the microphone output signals with the estimated feedback contributions portion removed. The at least one sound processor of certain embodiments is further configured to transmit the output signals to an actuator (e.g., actuator 458 of the actuating assembly 404) implanted on or within the recipient of the auditory prosthesis. The actuator is configured to generate stimulation signals and to provide the stimulation signals to a portion of the recipient's auditory system. The at least one sound processor of certain embodiments comprises a feedback controller (e.g., monitoring circuitry 420 and control circuitry 430) configured to monitor the one or more components of the auditory prosthesis (e.g., one or more of the signal processing circuitry 410, the processed data signals 412, and the at least one communication channel 414) and to provide control signals (e.g., filtering control signals 432) to the active feedback canceler in response at least in part to whether the one or more conditions exist.

In certain embodiments, the detected one or more error conditions include, but are not limited to, one or more of the following error conditions: instability of the signal processing circuitry 410 and/or the filtering circuitry 440; the signal processing circuitry 410 and/or filtering circuitry 440 using parameters that are outside one or more predetermined parameter ranges; the data signals 412 and/or filtering signals 442 having attributes outside one or more predetermined attribute ranges. One or more of these error conditions can be due to the absence of an operative communication channel between the at least one sound processor and the actuator (e.g., a communication channel successfully transmitting signals 456 from the apparatus 400 to an actuating assembly 404) and/or a proper communication channel (e.g., the signals 456 transmitted to the correct actuating assembly 404).

In certain embodiments, the at least one sound processor selects the operational state of the at least one sound processor by generating control signals which are transmitted to a portion of the auditory prosthesis. For example, the control signals can comprise filtering control signals 432 generated by the control circuitry 430 and transmitted to the filtering circuitry 440 to select an operational state of the filtering circuitry 440 of the at least one sound processor. Selecting the operational state of the filtering circuit 440 can include, but are not limited to, initiating a reset of the filtering circuit 440, temporarily stopping or halting operation of the filtering circuit 440, slowing an operational speed of the filtering circuit 440, changing a filtering type or mode being applied by the filtering circuit 440, placing the filtering circuit 440 temporarily in a safe mode (e.g., in which it utilizes a predetermined set of filter coefficient values corresponding to safe operation) or a sleep mode (e.g., in which it is not utilized to generate and transmit filtering signals 442 to the signal processing circuitry 410), and/or modifying one or more values (e.g., filter coefficient values) being utilized by the filtering circuitry 440 to generate the filtering signals 442 (e.g., commanding the filtering circuitry 440 to utilize a predetermined set of filter coefficient values obtained from a storage device in operable communication with the filtering circuitry 440; commanding the filtering circuitry 440 to utilize filter coefficient values obtained from another filtering circuitry of another auditory prosthesis of the bilateral recipient).

For another example, the control signals can comprise processing control signals 434 generated by the control circuitry 430 and transmitted to the signal processing circuitry 410 to select an operational state of the signal processing circuitry 410 of the at least one sound processor. Selecting the operational state of the signal processing circuitry 410 (e.g., the AGC 418) can include, but are not limited to, initiating a reset of the signal processing circuitry 410, temporarily stopping or halting operation of the signal processing circuitry 410, placing the signal processing circuitry 410 temporarily in a safe mode (e.g., in which it does not utilize the active feedback canceler) or a sleep mode (e.g., in which it is not utilized to generate and transmit data signals to the actuator), and/or modifying one or more values (e.g., gain values) being utilized by the signal processing circuitry 410 to generate the data signals 412 (e.g., reducing a gain applied by the signal processing circuit 410, changing a signal compression applied by the signal processing circuit 410; changing from using the microphone signals from a first microphone to using the microphone signals from a second microphone).

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

Certain Aspects

Certain aspects are listed below. The following aspects are presented for explanatory and illustrative purposes only. It will be appreciated that the foregoing description is not limited to the following aspects.

Aspect 1: A method comprising: detecting one or more operational states of an auditory prosthesis implanted on or within a recipient, the auditory prosthesis comprising a sound processor utilizing adaptive filtering circuitry to improve an acoustic response of the auditory prosthesis; and controlling the sound processor in response at least in part to said detected one or more operational states.

Aspect 2: The method of Aspect 1, wherein the one or more operational states comprises at least one of the following: an absence of a communication link between the sound processor and an implanted portion of the auditory prosthesis, a failure of the adaptive filtering circuitry to determine a set of filter coefficient values after a predetermined number of activity cycles, a set of filter coefficient values determined by the adaptive filtering circuitry that are outside a predetermined range of coefficient values, an instability of data signals outputted by the sound processor and transmitted to the implanted portion of the auditory prosthesis, and an instability of filtering signals generated by the adaptive filtering circuitry.

Aspect 3: The method of Aspect 2, wherein the implanted portion of the auditory prosthesis comprises an actuating assembly in operative communication with at least a portion of the auditory system of the recipient.

Aspect 4: The method of Aspect 3, wherein detecting the absence of the communication link comprises detecting an absence of a telemetry signal from the actuating assembly.

Aspect 5: The method of Aspect 3 or Aspect 4, wherein the communication link comprises communications between a first node of the sound processor and a second node of the actuating assembly, and said detecting the absence of the communication link comprises detecting consumption by the first node of at least one of an electric current and an electric power.

Aspect 6: The method of Aspect 5, wherein said detecting the absence of the communication link further comprises determining that the detected consumption is less than a predetermined consumption level.

Aspect 7: The method of Aspect 5, wherein said detecting the absence of the communication link further comprises accessing an estimated consumption level and determining that the detected consumption is less than the estimated consumption level.

Aspect 8: The method of any of Aspects 5 to 7, wherein the first node comprises a first radio-frequency (RF) antenna and the second node comprises a second RF antenna.

Aspect 9: The method of any of Aspects 5 to 7, wherein the first node comprises a first coil and the second node comprises a second coil, the second coil in inductive communication with the first coil.

Aspect 10: The method of any preceding Aspect, wherein said controlling comprises operating the sound processor to mitigate discomfort to the recipient.

Aspect 11: The method of any preceding Aspect, wherein said controlling comprises at least one of the following: changing an operational mode of the adaptive filtering circuitry, halting operation of the adaptive filtering circuitry, reducing an operation speed of the adaptive filtering circuitry, and changing values of one or more filter coefficients of the adaptive filtering circuitry.

Aspect 12: The method of Aspect 11, wherein said changing the values comprises changing the values to one or more predetermined values.

Aspect 13: The method of Aspect 11, wherein the auditory prosthesis comprises a first auditory prosthesis sub-system corresponding to a first ear of the recipient and a second auditory prosthesis sub-system corresponding to a second ear of the recipient, the first auditory prosthesis sub-system comprising the adaptive filtering circuitry and the second auditory prosthesis sub-system comprising a second adaptive filtering circuitry, said changing the values comprising changing the values to one or more values from the second adaptive filtering circuitry.

Aspect 14: The method of any preceding Aspect, wherein said controlling comprises changing an operational mode of the auditory prosthesis.

Aspect 15: The method of Aspect 14, wherein the auditory prosthesis comprises a first microphone and a second microphone, the first and second microphones configured to transmit microphone signals to the sound processor, wherein said one or more operational states are detected while the sound processor is using the microphone signals from the first microphone, and said changing an operational mode of the auditory prosthesis comprises switching the sound processor from using the microphone signals from the first microphone to using the microphone signals from the second microphone.

Aspect 16: The method of Aspect 15, wherein the first microphone is implanted on or within the recipient and the second microphone is external to the recipient, or the first microphone is external to the recipient and the second microphone is implanted on or within the recipient.

Aspect 17: The method of Aspect 15, wherein the auditory prosthesis comprises a first auditory prosthesis sub-system corresponding to a first ear of the recipient and a second auditory prosthesis sub-system corresponding to a second ear of the recipient, the first auditory prosthesis sub-system comprising the first microphone and the second auditory prosthesis sub-system comprising the second microphone.

Aspect 18: An apparatus comprising: signal processing circuitry configured to generate processed data signals in response at least in part to transducer signals from at least one acoustic transducer and filtering signals, and to transmit the processed data signals via at least one communication channel to an actuating assembly of an auditory prosthesis; monitoring circuitry configured to monitor one or more of the signal processing circuitry, the processed data signals, and the at least one communication channel, and to generate monitoring signals in response thereto; control circuitry configured to receive the monitoring signals and to generate filtering control signals in response at least in part thereto; and filtering circuitry configured to generate the filtering signals in response at least in part to the processed data signals and the filtering control signals.

Aspect 19: The apparatus of Aspect 18, wherein the at least one acoustic transducer comprises a microphone assembly of the auditory prosthesis, the microphone assembly configured to respond to sound received by the microphone assembly by generating the transducer signals to be indicative of the sound.

Aspect 20: The apparatus of Aspect 19, wherein the microphone assembly is implanted on or within a recipient.

Aspect 21: The apparatus of any of Aspects 18 to 20, wherein the at least one communication channel comprises at least one wireless link.

Aspect 22: The apparatus of Aspect 21, wherein the at least one wireless link comprises a radio-frequency link.

Aspect 23: The apparatus of Aspect 21, wherein the at least one wireless link comprises an inductive link.

Aspect 24: The apparatus of any of Aspects 18 to 23, wherein the actuating assembly of the auditory prosthesis comprises an actuator implanted on or within a recipient and is in operative communication with at least a portion of the recipient's auditory system, the actuator configured to respond to the processed data signals by generating stimulation signals and providing the stimulation signals to the portion of the recipient's auditory system.

Aspect 25: The apparatus of any of Aspects 18 to 24, wherein, in response to the monitoring signals being indicative of an error condition, the filtering control signals are configured to command the filtering circuitry to mitigate acoustic effects in the filtering signals due to the error condition.

Aspect 26: The apparatus of Aspect 25, wherein the error condition comprises at least one of the following error conditions: instability of the signal processing circuitry, the signal processing circuitry using signal processing parameters that are outside one or more predetermined parameter ranges, the processed data signals having attributes outside one or more predetermined attribute ranges, and absence of an operative communication channel.

Aspect 27: The apparatus of Aspect 25 or Aspect 26, wherein the filtering control signals are configured to command the filtering circuitry to enter a safe operational mode.

Aspect 28: The apparatus of Aspect 27, wherein the filtering circuitry in the safe operational mode is configured to utilize a predetermined set of filter coefficient values.

Aspect 29: The apparatus of Aspect 28, wherein the apparatus further comprises at least one storage device in operable communication with the filtering circuitry, the at least one storage device configured to communicate the predetermined set of filter coefficient values to the filtering circuitry.

Aspect 30: The apparatus of any of Aspects 18 to 29, wherein the control circuitry is further configured to, in response to the monitoring signals being indicative of an error condition, generate processing control signals and to transmit the processing control signals to the signal processing circuitry, the signal processing circuitry configured to respond to the processing control signals by mitigating the error condition.

Aspect 31: An apparatus comprising: at least one sound processor of an auditory prosthesis, the at least one sound processor configured to: receive microphone output signals from at least one microphone assembly of the auditory prosthesis, the microphone output signals indicative of sound received by the at least one microphone assembly; estimate a feedback contribution portion of the microphone output signals; detect one or more error conditions indicative of errors in the estimated feedback contribution portion; and select an operational state of the at least one sound processor in response to the detected one or more error conditions.

Aspect 32: The apparatus of Aspect 31, wherein the at least one sound processor comprises an active feedback canceler configured to estimate the feedback contribution portion of the microphone output signals and to generate estimation signals indicative of the estimated feedback contribution portion of the microphone output signals.

Aspect 33: The apparatus of Aspect 32, wherein the at least one sound processor comprises an adjustable gain controller configured to generate output signals in response at least in part to the microphone output signals and the estimation signals, the output signals indicative of the microphone output signals with the estimated feedback contribution portion removed.

Aspect 34: The apparatus of Aspect 33, wherein the at least one sound processor is further configured to transmit the output signals to an actuator implanted on or within a recipient of the auditory prosthesis, the actuator configured to generate stimulation signals and to provide the stimulation signals to a portion of the recipient's auditory system.

Aspect 35: The apparatus of any of Aspects 32 to 34, wherein the at least one sound processor comprises a feedback controller configured to monitor the one or more components of the auditory prosthesis and to provide control signals to the active feedback canceler in response at least in part to whether the one or more conditions exist.

What is claimed is:

1. An apparatus comprising:
    signal processing circuitry configured to generate processed data signals in response at least in part to transducer signals from at least one acoustic transducer and filtering signals, and to wirelessly transmit the processed data signals via at least one communication channel to an actuating assembly of an auditory prosthesis;
    monitoring circuitry configured to monitor one or more of the processed data signals and the at least one communication channel, and to generate monitoring signals in response thereto;
    control circuitry configured to receive the monitoring signals and to generate filtering control signals in response at least in part thereto; and
    filtering circuitry configured to generate the filtering signals in response at least in part to the processed data signals and the filtering control signals.

2. The apparatus of claim 1, wherein the at least one acoustic transducer comprises a microphone assembly of the auditory prosthesis, the microphone assembly configured to respond to sound received by the microphone assembly by generating the transducer signals to be indicative of the sound.

3. The apparatus of claim 2, wherein the microphone assembly is implanted on or within a recipient.

4. The apparatus of claim 1, wherein the at least one communication channel comprises at least one wireless link.

5. The apparatus of claim 4, wherein the at least one wireless link comprises a radio-frequency link.

6. The apparatus of claim 4, wherein the at least one wireless link comprises an inductive link.

7. The apparatus of claim 1, wherein the actuating assembly of the auditory prosthesis comprises an actuator implanted on or within a recipient and is in operative communication with at least a portion of the recipient's auditory system, the actuator configured to respond to the processed data signals by generating stimulation signals and providing the stimulation signals to the portion of the recipient's auditory system.

8. The apparatus of claim 1, wherein the monitoring circuitry is configured to monitor the at least one communication channel by detecting an absence of a telemetry signal from the actuating assembly.

9. The apparatus of claim 1, wherein the at least one communication channel comprises communications between a first node of the sound processor and a second node of the actuating assembly, the monitoring circuitry configured to monitor the at least one communication channel by detecting consumption by the first node of at least one of an electric current and an electric power.

10. The apparatus of claim 9, wherein the monitoring circuitry is further configured to monitor the at least one communication channel by determining that the detected consumption is less than a predetermined consumption level.

11. The apparatus of claim 9, wherein the monitoring circuitry is further configured to monitor the at least one communication channel by accessing an estimated consumption level and determining that the detected consumption is less than the estimated consumption level.

12. The apparatus of claim 9, wherein the first node comprises a first radio-frequency (RF) antenna and the second node comprises a second RF antenna.

13. The apparatus of claim 9, wherein the first node comprises a first coil and the second node comprises a second coil, the second coil in inductive communication with the first coil.

14. The apparatus of claim 1, wherein, in response to the monitoring signals being indicative of an error condition, the filtering control signals are configured to command the filtering circuitry to mitigate discomfort to the recipient.

15. The apparatus of claim 1, wherein, in response to the monitoring signals being indicative of an error condition, the filtering control signals are configured to command the filtering circuitry to perform at least one of the following: changing an operational mode of the filtering circuitry, halting operation of the filtering circuitry, reducing an operation speed of the filtering circuitry, and changing values of one or more filter coefficients of the filtering circuitry.

16. The apparatus of claim 15, wherein said changing the values comprises changing the values to one or more predetermined values.

17. The apparatus of claim 15, wherein the auditory prosthesis comprises a first auditory prosthesis sub-system corresponding to a first ear of a recipient and a second auditory prosthesis sub-system corresponding to a second ear of the recipient, the first auditory prosthesis sub-system comprising the filtering circuitry and the second auditory prosthesis sub-system comprising a second filtering circuitry, said changing the values comprising changing the values to one or more values from the second filtering circuitry.

18. The apparatus of claim 1, wherein, in response to the monitoring signals being indicative of an error condition, the filtering control signals are configured to command the filtering circuitry to change an operational mode of the auditory prosthesis.

19. The apparatus of claim 18, wherein the auditory prosthesis comprises a first microphone and a second microphone, the first and second microphones configured to transmit microphone signals to the signal processing circuitry, wherein the monitoring circuitry is configured to generate the monitoring signals while the signal processing circuitry is using the microphone signals from the first microphone, and changing the operational mode of the auditory prosthesis comprises switching the signal processing circuitry from using the microphone signals from the first microphone to using the microphone signals from the second microphone.

20. The apparatus of claim 19, wherein the first microphone is implanted on or within a recipient and the second microphone is external to the recipient, or the first microphone is external to the recipient and the second microphone is implanted on or within the recipient.

21. The apparatus of claim 19, wherein the auditory prosthesis comprises a first auditory prosthesis sub-system corresponding to a first ear of a recipient and a second auditory prosthesis sub-system corresponding to a second ear of the recipient, the first auditory prosthesis sub-system comprising the first microphone and the second auditory prosthesis sub-system comprising the second microphone.

22. An apparatus comprising:
signal processing circuitry configured to generate processed data signals in response at least in part to transducer signals from at least one acoustic transducer and filtering signals, and to transmit the processed data signals via at least one communication channel to an actuating assembly of an auditory prosthesis;
monitoring circuitry configured to monitor one or more of the signal processing circuitry, the processed data signals, and the at least one communication channel, and to generate monitoring signals in response thereto;
control circuitry configured to receive the monitoring signals and to generate filtering control signals in response at least in part thereto; and
filtering circuitry configured to generate the filtering signals in response at least in part to the processed data signals and the filtering control signals, wherein, in response to the monitoring signals being indicative of an error condition, the filtering control signals are configured to command the filtering circuitry to mitigate acoustic effects in the filtering signals due to the error condition.

23. The apparatus of claim 22, wherein the error condition comprises at least one of the following error conditions: instability of the signal processing circuitry, the signal processing circuitry using signal processing parameters that are outside one or more predetermined parameter ranges, the processed data signals having attributes outside one or more predetermined attribute ranges, and absence of an operative communication channel.

24. The apparatus of claim 22, wherein the filtering control signals are configured to command the filtering circuitry to enter a safe operational mode.

25. The apparatus of claim 24, wherein the filtering circuitry in the safe operational mode is configured to utilize a predetermined set of filter coefficient values.

26. The apparatus of claim 25, wherein the apparatus further comprises at least one storage device in operable communication with the filtering circuitry, the at least one storage device configured to communicate the predetermined set of filter coefficient values to the filtering circuitry.

27. An apparatus comprising:
signal processing circuitry configured to generate processed data signals in response at least in part to transducer signals from at least one acoustic transducer and filtering signals, and to transmit the processed data signals via at least one communication channel to an actuating assembly of an auditory prosthesis;
monitoring circuitry configured to monitor one or more of the signal processing circuitry, the processed data signals, and the at least one communication channel, and to generate monitoring signals in response thereto;
control circuitry configured to receive the monitoring signals and to generate filtering control signals in response at least in part thereto; and
filtering circuitry configured to generate the filtering signals in response at least in part to the processed data signals and the filtering control signals, wherein the control circuitry is further configured to, in response to the monitoring signals being indicative of an error condition, generate processing control signals and to transmit the processing control signals to the signal processing circuitry, the signal processing circuitry configured to respond to the processing control signals by mitigating the error condition.

28. An apparatus comprising:
signal processing circuitry configured to generate processed data signals in response at least in part to transducer signals from at least one acoustic transducer and filtering signals, and to transmit the processed data signals via at least one communication channel to an actuating assembly of an auditory prosthesis;
monitoring circuitry configured to monitor one or more of the signal processing circuitry, the processed data signals, and the at least one communication channel, and to generate monitoring signals in response thereto;
control circuitry configured to receive the monitoring signals and to generate filtering control signals in response at least in part thereto; and
filtering circuitry configured to generate the filtering signals in response at least in part to the processed data signals and the filtering control signals, wherein the signal processing circuitry comprises at least one sound processor of an auditory prosthesis, the at least one acoustic transducer comprises at least one microphone assembly, and the transducer signals comprise microphone output signals, the at least one sound processor configured to receive the microphone output signals from the at least one microphone assembly of the auditory prosthesis, the microphone output signals indicative of sound received by the at least one microphone assembly, the filtering circuitry configured to estimate a feedback contribution portion of the microphone output signals, the monitoring circuitry configured to detect one or more error conditions indicative of errors in the estimated feedback contribution portion, and the control circuitry configured to select an operational state of the at least one sound processor in response to the detected one or more error conditions.

29. The apparatus of claim 28, wherein the at least one sound processor comprises an active feedback canceler configured to estimate the feedback contribution portion of the microphone output signals and to generate estimation signals indicative of the estimated feedback contribution portion of the microphone output signals.

30. The apparatus of claim 29, wherein the at least one sound processor comprises an adjustable gain controller configured to generate output signals in response at least in part to the microphone output signals and the estimation signals, the output signals indicative of the microphone output signals with the estimated feedback contribution portion removed.

31. The apparatus of claim 30, wherein the at least one sound processor is further configured to transmit the output signals to an actuator implanted on or within a recipient of the auditory prosthesis, the actuator configured to generate stimulation signals and to provide the stimulation signals to a portion of the recipient's auditory system.

32. The apparatus of claim 29, wherein the at least one sound processor comprises a feedback controller configured to monitor the one or more components of the auditory prosthesis and to provide control signals to the active feedback canceler in response at least in part to whether the one or more conditions exist.

* * * * *